(12) United States Patent
Bauer et al.

(10) Patent No.: US 7,718,686 B2
(45) Date of Patent: May 18, 2010

(54) IMIDAZOLE VARIANTS AS MODULATORS OF GABA RECEPTOR FOR THE TREATMENT OF GI DISORDERS

(75) Inventors: Udo Bauer, Mölndal (SE); Wayne Brailsford, Mölndal (SE); Vijay Chhajlani, Wilmington, DE (US); Bryan Egner, Mölndal (SE); Ola Fjellström, Mölndal (SE); Linda Gustafsson, Mölndal (SE); Jan Mattsson, Mölndal (SE); Karolina Nilsson, Mölndal (SE); Thomas Olsson, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 621 days.

(21) Appl. No.: 11/570,830

(22) PCT Filed: Jun. 20, 2005

(86) PCT No.: PCT/SE2005/000951

§ 371 (c)(1),
(2), (4) Date: Dec. 18, 2006

(87) PCT Pub. No.: WO2006/001750

PCT Pub. Date: Jan. 5, 2006

(65) Prior Publication Data

US 2008/0269216 A1    Oct. 30, 2008

(30) Foreign Application Priority Data

Jun. 24, 2004  (SE) .................................. 0401653

(51) Int. Cl.
*A61K 31/4172* (2006.01)
*C07D 233/66* (2006.01)
(52) U.S. Cl. .................................. 514/398; 548/326.5
(58) Field of Classification Search .............. 548/326.5; 514/398
See application file for complete search history.

(56) References Cited

U.S. PATENT DOCUMENTS

| 3,876,655 | A  | 4/1975  | Heyes et al. |
| 4,659,720 | A  | 4/1987  | Chabala et al. |
| 5,162,364 | A  | 11/1992 | Debaert et al. |
| 5,214,063 | A  | 5/1993  | Debaert et al. |
| 5,278,166 | A  | 1/1994  | Debaert et al. |
| 5,304,685 | A  | 4/1994  | Merger et al. |
| 2004/0259883 | A1 | 12/2004 | Sakashita et al. |
| 2008/0262064 | A1 | 10/2008 | Bauer et al. |
| 2008/0269216 | A1 | 10/2008 | Bauer et al. |
| 2008/0312291 | A1 | 12/2008 | Bauer et al. |
| 2008/0312305 | A1 | 12/2008 | Bauer et al. |
| 2009/0005428 | A1 | 1/2009  | Bauer et al. |
| 2009/0023704 | A1 | 1/2009  | Cheng et al. |
| 2009/0062365 | A1 | 3/2009  | Bauer et al. |
| 2009/0149474 | A1 | 6/2009  | Bauer et al. |

FOREIGN PATENT DOCUMENTS

| CH | 449 046 | 7/1963 |
| EP | 0 269 238 A1 | 6/1988 |
| EP | 0 181 833 B1 | 5/1990 |
| EP | 0 356 128 B1 | 7/1992 |
| EP | 0 399 949 B1 | 4/1995 |
| FR | 2 722 192 | 1/1996 |
| WO | WO 94/19351 | 9/1994 |
| WO | WO 97/31900 | 9/1997 |
| WO | WO 98/11885 | 3/1998 |
| WO | WO 01/41743 A1 | 6/2001 |
| WO | WO 01/42252 A1 | 6/2001 |
| WO | WO 01/90141 A3 | 11/2001 |
| WO | WO-02/00651 A2 * | 1/2002 |
| WO | WO 03/090731 A1 | 11/2003 |
| WO | WO-2006/001750 A1 | 1/2006 |

OTHER PUBLICATIONS

Binet et al., "The Heptahelical Domain of $GABA_{B2}$ is Activated Directly by CGP7930, a Positive Allosteric Modulator of the $GABA_B$ Receptor", Journal of Biological Chemistry 2004, 279(28), 29085-91.

Onali et al., "Positive Regulation of $GABA_B$ Receptors Dually Coupled to Cyclic AMP by the Allosteric Agent CGP7930", European Journal of Pharmacology 2003, 471(2), 77-84.

(Continued)

*Primary Examiner*—Kamal A Saeed
*Assistant Examiner*—Janet L Coppins
(74) *Attorney, Agent, or Firm*—White & Case LLP

(57) ABSTRACT

The present invention relates to novel compounds having a positive allosteric GABAB receptor (GDR) modulator effect, methods for the preparation of said compounds and to their use, optionally in combination with a GABAB agonist, for the inhibition of transient lower esophageal sphincter relaxations, for the treatment of gastroesophageal reflux disease, as well as for the treatment of functional gastrointestinal disorders and irritable bowel syndrome (IBS). A compound of the general formula I.

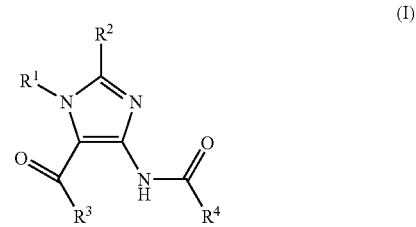

(I)

26 Claims, No Drawings

OTHER PUBLICATIONS

Pin et al., "Positive Allosteric Modulators for γ-Aminobutyric Acid$_B$ Receptors Open New Routes for the Development of Drugs Targeting Family 3 G-Protein-Coupled Receptors", Molecular Pharmacology, 2001, 60(5), 881-4.

Lidums et al., "Control of Transient Lower Esophageal Sphincter Relaxations and Reflux by the GABA$_B$ Agonist Baclofen in Normal Subjects", Gastroenterology 2000, 118, 7-13.

Holloway, Richard, "Systematic Pharmacomodulation of Transient Lower Esophageal Sphincter Relaxations", Am. J. Med., 2001, 111(8A), 178s-185s.

Kerr et al., "Arylalkylamines are a Novel Class of Positive Allosteric Modulators at GABA$_B$ Receptors in Rat Neocortex", European Journal of Pharmacology 2002, 451(1), 69-77.

Soudijn et al., "Allosteric Modulation of G Protein-Coupled Receptors", Current Opinion in Drug Discovery and Development 2002, 5(5), 749-55.

Urwyler et al., "N,N'-Dicyclopentyl-2-methylsulfanyl-5-nitro-pyrimidine-4, 6-diamine (GS39783) and Structurally Related Compounds: Novel Allosteric Enhancers of γ-Aminobutyric Acid$_B$ Receptor Function", The Journal of Pharmacology and Experimental Therapeutics, 307 (2003), 322-330.

Gompper et al, Tetrahedron Lett. (1966), 1885-1889.

Nielsen et al., "Phosphorus Pentoxide-Amine Hydrochloride Mixtures as Reagents in a New Synthesis of Hypoxanthines", Tetrahedron (1982), 38: 1435-1441.

Gewald et al., "4-Amino-imidazole durch *Thorpe*-Cyclisierung", Monatshefte für Chemie (1976), 107: 1413-1421.

Soudijn et al., "Expert Opinion" Ther. Patents (2001), 11, 1889-1904.

Mittal et al., "Transient Lower Esophageal Sphincter Relaxation." Gastroenterology (1995) 109, pp. 601-610.

Van Heerwaarden et al., "Diagnosis of reflux disease", Baillière's Clin. Gastroenterol. 2000, 14, pp. 759-774.

Ludovici et al., "Evolution of Anti-HIV Drug Candidates, Part 1: From α-Anilinophenylacetamide (α-APA) to Imidoyl Thiourea (ITU)", Bioorg. Med. Chem. Lett. 2001, 11, 2225-2228.

McAtee et al., "Novel Substituted 4-phenyl-[1,3]dioxanes: Potent and Selective Orexin Receptor 2 (OX$_2$R) Antagonists", Bioorg. Med. Chem. Lett. 2004, 14, 4225-4229.

Coward et al., "Chimeric G Proteins Allow a High-Throughput Signaling Assay of G$_1$-Coupled Receptors", Anal. Biochem. (1999) 270, 242-248.

Thompson et al., "Functional Bowel Disorders and Functional Abdominal Pain". In: Drossman et al, eds. Rome II: Functional Gastrointestinal Disorders: Diagnosis, Pathophysiology and Treatment. 2 ed. McLean, VA: Degnon Associates, Inc.; 2000: 351-432.

Drossman et al. Rome II: A multinational consensus document on Functional Gastrointestinal Disorders, Gut, 1999, 45 (Suppl. 2), II I-II 81, Sep. 1, 1999.

Froestl et al., "Phosphinic Acid Analogues of GABA. 1. New Potent and Selective GABA$_S$ Agonists", J. Med. Chem. (1995), 38, 3297-3312.

Carruthers et al., "Synthesis of a Series of Sulfinic Acid Analogs of GABA and Evaluation of Their GABA$_B$ Receptor Affinities", Bioorg. & Med. Chem. Lett. (1998), 8, 3059-3064.

Kerr et al., "Metabotropic GABA$_B$ Receptors: New Challenges in Drug Design", Curr. Med. Chem.-Central Nervous System Agents (2001), 1, 27-42.

Urwyler et al,, "Positive Allosteric Modulation of Native and Recombinant γ-Aminobutyric Acid$_B$ Receptors by 2, 6-Di-*tert*-butyl-4-(3-hydroxy-2,2-dimethyl-propyl)-phenol (CGP7930) and its Aldehyde Analog CGP13501", Society for Neuroscience, 30th Annual Meeting, New Orleans, La., Nov. 4-9, 2000: Positive Allosteric Modulation of Native and Recombinant GABAB Receptor Activity, S. Urwyler et al.; Molecular Pharmacol. (2001), 60, 963-971.

Holloway et al., Gastroenterol. Clin. N. Amer. 1990, 19, 517-535.

Brice et al, "Metabotropic glutamate and GABA$_B$ receptors contribute to the modulation of glucose-stimulated insulin secretion in pancreatic beta cells," Diabetologia, 2002, 45, p. 242-52.

Krogsgaard-Larsen et al.: "GABA$_A$ and GABA$_B$ receptor agonists, partial agonists, antagonists and modulators: design and therapeutic prospects," Eur. J. Pharm. Sci. 1997, (5), 355-84.

Bream et al., European Journal of Medicinal Chemistry (1981), 16, 175-179.

Henze et al., Journal of Organic Chemistry (1953), 18, 653-656.

D. L. Huges in Organic Reactions, vol. 42, p. 335-656 (1992).

Huppatz, Australian J. Chem. (1985), 38, 221-230.

Rappoport et al., J. Org. Chem. (1982), 47, 1397-1408.

Ried et al., Chemische Berichte (1983), 116, 1547.

Ried et al., Liebigs Annalen der Chemie (1986), 4, 780.

Schmidt et al., Helvetica Chimica Acta (1959), 42, 349-359.

Shiori, J. Org. Chem. (1978), 43, 3631-3632.

Slätt et al., Journal of Heterocyclic Chemistry (2005), 42, 141-145.

STN International, file CAPLUS, CAPLUS Accession No. 1982:616123, Document No. 97:216123, Nielsen, F.E. et al. "Phosphorous pentoxide in organic synthesis. 1. Phosphorous pentoxide-amine hydrochloride mixtures as reagents in a new synthesis of hypoxanthines", Tetrahedron (1982), 38, (10), p. 1435-1441.

STN International, file CAPLUS, CAPLUS Accession No. 2002:10470, Document No. 136:85810, DuPont Pharmaceuticals Company "Preparation of arylamides and heterocyclylamides as factor Xa inhibitors for treatment of thromboembolic disorders"; WO 2002/000651 A2, 20020103.

Lwowski, Synthesis (1971), 5, 263.

Yu et al., Synthesis (2004), 7, 1021-1028.

Golankiewicz et al., Tetrahedron (1985), 41, 5989-5994.

Yadav et al., European Journal of Organic Chemistry (2005), 2, 452-456.

Zimmerman et al., Journal of Organic Chemistry (1989), 54, 1256-1264.

* cited by examiner

IMIDAZOLE VARIANTS AS MODULATORS OF GABA RECEPTOR FOR THE TREATMENT OF GI DISORDERS

FIELD OF THE INVENTION

The present invention relates to novel compounds having a positive allosteric $GABA_B$ receptor (GBR) modulator effect, methods for the preparation of said compounds and their use for the inhibition of transient lower esophageal sphincter relaxations, for the treatment of gastroesophageal reflux disease, as well as for the treatment of functional gastrointestinal disorders and irritable bowel syndrome (IBS).

BACKGROUND OF THE INVENTION

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastroesophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, recent research (e.g. Holloway & Dent (1990) *Gastroenterol. Clin. N. Amer.* 19, pp. 517-535) has shown that most reflux episodes occur during transient lower esophageal sphincter relaxations (TLESR), i.e. relaxations not triggered by swallows. It has also been shown that gastric acid secretion usually is normal in patients with GERD.

Consequently, there is a need for a therapy that reduces the incidence of TLESR and thereby prevents reflux.

$GABA_B$-receptor agonists have been shown to inhibit TLESR, which is disclosed in WO 98/11885 A1.

Functional gastrointestinal disorders, such as functional dyspepsia, can be defined in accordance with Thompson W G, Longstreth G F, Drossman D A, Heaton K W, Irvine E J, Mueller-Lissner S A. *C. Functional Bowel Disorders and Functional Abdominal Pain*. In: Drossman D A, Talley N J, Thompson W G, Whitehead W E, Coraziarri E, eds. *Rome II: Functional Gastrointestinal Disorders: Diagnosis, Pathophysiology and Treatment*. 2 ed. McLean, V A: Degnon Associates, Inc.; 2000:351-432 and Drossman D A, Corazziari E, Talley N J, Thompson W G and Whitehead W E. *Rome II: A multinational consensus document on Functional Gastrointestinal Disorders*. Gut 45(Suppl.2), II1-II81. Sep. 1, 1999.

Irritable bowel syndrome (IBS) can be defined in accordance with Thompson W G, Longstreth G F, Drossman D A, Heaton K W, Irvine E J, Mueller-Lissner S A. *C. Functional Bowel Disorders and Functional Abdominal Pain*. In: Drossman D A, Talley N J, Thompson W G, Whitehead W E, Coraziarri E, eds. *Rome II: Functional Gastrointestinal Disorders: Diagnosis, Pathophysiology and Treatment*. 2 ed. McLean, V A: Degnon Associates, Inc.; 2000:351-432 and Drossman D A, Corazziari E, Talley N J, Thompson W G and Whitehead W E. *Rome II: A multinational consensus document on Functional Gastrointestinal Disorders*. Gut 45(Suppl.2), II1-II81. Sep. 1, 1999.

$GABA_B$ Receptor Agonists

GABA (4-aminobutanoic acid) is an endogenous neurotransmitter in the central and peripheral nervous systems. Receptors for GABA have traditionally been divided into $GABA_A$ and $GABA_B$ receptor subtypes. $GABA_B$ receptors belong to the superfamily of G-protein coupled receptors (GPCRs).

The most studied GABAB receptor agonist baclofen (4-amino-3-(p-chlorophenyl)butanoic acid; disclosed in CH 449046) is useful as an antispastic agent. EP 356128 A2 describes the use of the $GABA_B$ receptor agonist (3-aminopropyl)methylphosphinic acid for use in therapy, in particular in the treatment of central nervous system disorders.

EP 463969 A1 and FR 2722192 A1 disclose 4-aminobutanoic acid derivatives having different heterocyclic substituents at the 3-carbon of the butyl chain. EP 181833 A1 discloses substituted 3-aminopropylphosphinic acids having high affinities towards $GABA_B$ receptor sites. EP 399949 A1 discloses derivatives of (3-aminopropyl)methylphosphinic acid, which are described as potent $GABA_B$ receptor agonists. Still other (3-aminopropyl)methylphosphinic acids and (3-aminopropyl)phosphinic acids have been disclosed in WO 01/41743 A1 and WO 01/42252 A1, respectively. Structure-activity relationships of several phosphinic acid analogues with respect to their affinities to the $GABA_B$ receptor are discussed in *J. Med. Chem.* (1995), 38, 3297-3312. Sulphinic acid analogues and their $GABA_B$ receptor activities are described in *Bioorg. & Med. Chem. Lett.* (1998), 8, 3059-3064. For a more general review on $GABA_B$ ligands, see *Curr. Med. Chem.—Central Nervous System Agents* (2001), 1, 27-42.

Positive Allosteric Modulation of $GABA_B$ Receptors 2,6-Di-tert-butyl-4-(3-hydroxy-2,2-dimethylpropyl)phenol (CGP7930) and 3-(3,5-di-tert-butyl-4-hydroxyphenyl)-2,2-dimethylpropanal (disclosed in U.S. Pat. No. 5,304,685) have been described to exert positive allosteric modulation of native and recombinant $GABA_B$ receptor activity (Society for Neuroscience, 30th Annual Meeting, New Orleans, La., Nov. 4-9, 2000: *Positive Allosteric Modulation of Native and Recombinant $GABA_B$ Receptor Activity*, S. Urwyler et al.; *Molecular Pharmacol.* (2001), 60, 963-971).

N,N-Dicyclopentyl-2-methylsulfanyl-5-nitro-pyrimidine-4,6-diamine has been described to exert positive allosteric modulation of the GABAB receptor (The Journal of Pharmacology and Experimental Therapeutics, 307 (2003), 322-330).

1H-imidazole-5-carboxylic Acid Derivatives

A few 4-amino-1H-imidazole-5-carboxylic acid ethyl esters are disclosed as intermediates for the synthesis of purines (*Tetrahedron Lett.* (1966), 1885-1889) or imidazo[4,5-d]pyrimidones and imidazo[4,5,-b]pyridines (*Monatshefte für Chemie* (1976), 107:1413-1421). Also, 1,7-dihydro-6H-purine-6-ones are prepared from 4-acylamino-1H-imidazole-5-carboxylic acid ethyl esters (*Tetrahedron* (1982), 38:1435-1441). However, these compounds are not known as positive allosteric modulators of the $GABA_B$ receptor and have not been described as being useful for the treatment of GERD or functional gastrointestinal disorders.

For a recent review on allosteric modulation of GPCRs, see: *Expert Opin. Ther. Patents* (2001), 11, 1889-1904.

OUTLINE OF THE INVENTION

The present invention provides novel compounds of formula I:

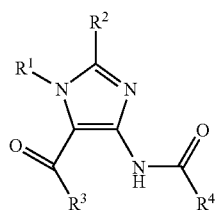

(I)

wherein

R¹ represents $C_1$-$C_{10}$ alkyl; $C_2$-$C_{10}$ alkenyl; $C_2$-$C_{10}$ alkynyl; or $C_3$-$C_{10}$ cycloalkyl, each optionally and independently substituted by $C_1$-$C_{10}$ alkoxy, $C_3$-$C_{10}$ cycloalkyl, $C_1$-$C_{10}$ thioalkoxy, halogen, hydroxy, mercapto, carboxylic acid, carboxylic acid ester, carboxylic acid amide, nitrile or one or two aryl or heteroaryl groups;

aryl or heteroaryl, each optionally and independently substituted by $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, nitrile or one or two aryl or heteroaryl groups;

R² represents $C_1$-$C_{10}$ alkoxy or $C_1$-$C_{10}$ thioalkoxy, each optionally and independently substituted by $C_1$-$C_{10}$ thioalkoxy, halogen, hydroxy, mercapto, carboxylic acid, carboxylic acid ester, carboxylic acid amide, nitrile or one or two aryl or heteroaryl groups;

R³ represents $C_1$-$C_{10}$ alkoxy, optionally substituted by $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, nitrile or one or two aryl or heteroaryl groups;

$C_1$-$C_{10}$ alkyl; $C_2$-$C_{10}$ alkenyl; $C_2$-$C_{10}$ alkynyl; or $C_3$-$C_{10}$ cycloalkyl, each optionally and independently substituted by $C_1$-$C_{10}$ alkoxy, $C_3$-$C_{10}$ cycloalkyl, keto, $C_1$-$C_{10}$ thioalkoxy, halogen, hydroxy, mercapto, carboxylic acid, carboxylic acid ester, carboxylic acid amide, nitrile or one or two aryl or heteroaryl groups;

aryl or heteroaryl, each optionally and independently substituted by $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, nitrile or one or two aryl or heteroaryl groups; or amino, optionally mono- or disubstituted with $C_1$-$C_{10}$ alkyl, $C_2$-$C_{10}$ alkenyl, $C_2$-$C_{10}$ alkynyl or $C_3$-$C_{10}$ cycloalkyl;

R⁴ represents $C_1$-$C_{10}$ alkyl; $C_2$-$C_{10}$ alkenyl; $C_2$-$C_{10}$ alkynyl; $C_1$-$C_{10}$ alkoxy; or $C_3$-$C_{10}$ cycloalkyl, each optionally and independently substituted by $C_1$-$C_{10}$ alkoxy, $C_3$-$C_{10}$ cycloalkyl, $C_1$-$C_{10}$ thioalkoxy, halogen, hydroxy, mercapto, carboxylic acid, carboxylic acid ester, carboxylic acid amide, nitrile or one or two aryl or heteroaryl groups;

aryl or heteroaryl, each optionally and independently substituted by $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, nitrile or one or two aryl or heteroaryl groups;

with the exceptions of:
1H-imidazole-5-carboxylic acid, 4-(acetylamino)-1-methyl-2-(methylthio)-, ethyl ester;
1H-imidazole-5-carboxylic acid, 4-(acetylamino)-2-(methylthio)-1-phenyl-, ethyl ester;
1H-imidazole-5-carboxylic acid, 4-[(4-chlorobenzoyl)amino]-1-(2-furanylmethyl)-2-(methylthio)-, ethyl ester;
1H-imidazole-5-carboxylic acid, 4-(acetylamino)-1-(2-furanylmethyl)-2-(methylthio)-, ethyl ester;
1H-imidazole-5-carboxylic acid, 4-(acetylamino)-2-(methylthio)-1-(2-thienylmethyl)-, ethyl ester;
1H-imidazole-5-carboxylic acid, 2-(methylthio)-4-[[(5-nitro-2-furanyl)carbonyl]amino]-1-(2-thienylmethyl)-, ethyl ester;
1H-imidazole-5-carboxylic acid, 4-[[4-(1,1-dimethylethyl)benzoyl]amino]-1-(2-methoxyphenyl)-2-(methylthio)-, ethyl ester;
1H-imidazole-5-carboxylic acid, 4-[(2,4-dichlorobenzoyl)amino]-1-[4-(1-methylethyl)phenyl]-2-(methylthio)-, ethyl ester;
1H-imidazole-5-carboxylic acid, 1-[4-(1-methylethyl)phenyl]-4-[(2-methyl-1-oxopropyl)amino]-2-(methylthio)-, ethyl ester;
1H-imidazole-5-carboxylic acid, 1-[2-thienylmethyl]-4-[(chloro-acetyl)amino]-2-(methylthio)-, ethyl ester;
1H-imidazole-5-carboxylic acid, 1-[2-thienylmethyl]-4-[(dichloro-acetyl)amino]-2-(methylthio)-, ethyl ester; and
1H-imidazole-5-carboxylic acid, 1-[2-methoxyphenyl]-4-[(trichloro-acetyl)amino]-2-(methylthio)-, ethyl ester.

In one embodiment of the present invention, R² is $C_1$-$C_{10}$ alkoxy, optionally substituted by $C_1$-$C_{10}$ thioalkoxy, halogen, hydroxy, mercapto, carboxylic acid, carboxylic acid ester, carboxylic acid amide, nitrile or one or two aryl or heteroaryl groups.

In a further embodiment of the invention, R² is $C_1$-$C_{10}$ thioalkoxy, optionally substituted by $C_1$-$C_{10}$ thioalkoxy, halogen, hydroxy, mercapto, carboxylic acid, carboxylic acid ester, carboxylic acid amide, nitrile or one or two aryl or heteroaryl groups.

This new class of compounds, of formula I above, 1H-imidazole-5-carboxylic acid ethyl esters or amides, are useful as positive allosteric $GABA_B$ receptor modulators.

The general terms used in the definition of formula I have the following meanings:

$C_1$-$C_{10}$ alkyl is a straight or branched alkyl group, having from 1 to 10 carbon atoms, for example methyl, ethyl, n-propyl, isopropyl, n-butyl, isobutyl, secondary butyl, tertiary butyl, pentyl, isopentyl, hexyl or heptyl. The alkyl may be substituted by one or more of $C_1$-$C_{10}$ alkoxy, $C_1$-$C_{10}$ thioalkoxy, halogen, hydroxy, mercapto, carboxylic acid, carboxylic acid ester, carboxylic acid amide, nitrile or one or two aryl or heteroaryl groups. The alkyl groups may contain one or more heteroatoms selected from O, N and S, i.e. one or more of the carbon atoms may be substituted by such a heteroatom. Examples of such groups are methyl-ethylether, methyl-ethylamine and methyl-thiomethyl. The alkyl group may form part of a ring. One or more of the hydrogen atoms of the alkyl group may be substituted for a fluorine atom.

$C_2$-$C_{10}$ alkenyl is a straight or branched alkenyl group, having 2 to 10 carbon atoms, for example vinyl, isopropenyl and 1-butenyl. The alkenyl may be substituted by one or more of $C_1$-$C_{10}$ alkoxy, $C_1$-$C_{10}$ thioalkoxy, halogen, hydroxy, mercapto, carboxylic acid, carboxylic acid ester, carboxylic acid amide, nitrile or one or two aryl or heteroaryl groups. The alkenyl groups may contain one or more heteroatoms selected from O, N and S, i.e. one or more of the carbon atoms may be substituted by such a heteroatom. One or more of the hydrogen atoms of the alkenyl group may be substituted for a fluorine atom.

$C_2$-$C_{10}$ alkynyl is a straight or branched alkynyl group, having 2 to 10 carbon atoms, for example ethynyl, 2-propynyl and but-2-ynyl. The alkynyl may be substituted by one or more of $C_1$-$C_{10}$ alkoxy, $C_1$-$C_{10}$ thioalkoxy, halogen, hydroxy, mercapto, carboxylic acid, carboxylic acid ester, carboxylic acid amide, nitrile or one or two aryl or heteroaryl groups. The alkynyl groups may contain one or more heteroatoms selected from O, N and S, i.e. one or more of the carbon atoms may be substituted by such a heteroatom. One or more of the hydrogen atoms of the alkynyl group may be substituted for a fluorine atom.

$C_3$-$C_{10}$ cycloalkyl is a cyclic alkyl, having 3 to 10 carbon atoms such as cyclopropyl, cyclobutyl, cyclopentyl or cyclohexyl. The cycloalkyl may also be unsaturated. The cycloalkyl may be substituted by one or more of $C_1$-$C_{10}$ alkoxy, $C_1$-$C_{10}$ thioalkoxy, halogen, hydroxy, mercapto, carboxylic acid, carboxylic acid ester, carboxylic acid amide, nitrile or one or two aryl or heteroaryl groups. The cycloalkyl groups may have one or more heteroatoms selected from O, N and S, i.e. one or more of the carbon atoms may be substituted by such a heteroatom. One or more of the hydrogen atoms of the cycloalkyl group may be substituted for a fluorine atom.

$C_1$-$C_{10}$ alkoxy is an alkoxy group having 1 to 10 carbon atoms, for example methoxy, ethoxy, n-propoxy, n-butoxy, isopropoxy, isobutoxy, secondary butoxy, tertiary butoxy, pentoxy, hexoxy or a heptoxy group. The alkoxy may be cyclic, partially unsaturated or unsaturated, such as in propenoxy or cyclopentoxy. The alkoxy may be aromatic, such as in benzyloxy or phenoxy. The alkoxy groups may contain one or more heteroatoms selected from O, N and S, i.e. one or more of the carbon atoms may be substituted by such a heteroatom. The alkoxy may be substituted by one or more of $C_1$-$C_{10}$ alkoxy, $C_1$-$C_{10}$ thioalkoxy, halogen, hydroxy, mercapto, carboxylic acid, carboxylic acid ester, carboxylic acid amide, nitrile or one or two aryl or heteroaryl groups.

$C_1$-$C_{10}$ thioalkoxy is a thioalkoxy group having 1 to 10 carbon atoms, for example thiomethoxy, thioethoxy, n-thiopropoxy, n-thiobutoxy, thioisopropoxy, thioisobutoxy, secondary thiobutoxy, tertiary thiobutoxy, thiopentoxy, thiohexoxy or thioheptoxy group. The thioalkoxy may be unsaturated, such as in thiopropenoxy or aromatic, such as in thiobenzyloxy or thiophenoxy. The thioalkoxy may be substituted by one or more of $C_1$-$C_{10}$ alkoxy, $C_1$-$C_{10}$ thioalkoxy, halogen, hydroxy, mercapto, carboxylic acid, carboxylic acid ester, carboxylic acid amide, nitrile or one or-two aryl or heteroaryl groups.

The term aryl is herein defined as an aromatic ring having from 6 to 14 carbon atoms including both single rings and polycyclic compounds, such as phenyl, benzyl or naphtyl, optionally substituted by one or more substituents such as $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, nitrile, or one or two aryl or heteroaryl groups, such as in biphenyl. Polycyclic rings are saturated, partially unsaturated or saturated.

The term heteroaryl is herein defined as an aromatic ring having 3 to 14 carbon atoms, including both single rings and polycyclic compounds in which one or several of the ring atoms is either oxygen, nitrogen or sulphur, such as furanyl, thiophenyl or imidazopyridine. The heteroaryl is optionally substituted by one or more substituents such as $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, nitrile or one or two aryl or heteroaryl groups, such as in biphenyl. Polycyclic rings are saturated, partially unsaturated or saturated. Halogen as used herein is selected from chlorine, fluorine, bromine or iodine.

When the compounds of formula I have at least one asymmetric carbon atom, they can exist in several stereochemical forms. The present invention includes the mixture of isomers as well as the individual stereoisomers. The present invention further includes geometrical isomers, rotational isomers, enantiomers, racemates and diastereomers.

Where applicable, the compounds of formula I may be used in neutral form, e.g. as a carboxylic acid, or in the form of a salt, preferably a pharmaceutically acceptable salt such as the sodium, potassium, ammonium, calcium or magnesium salt of the compound at issue.

The compounds of formula I are useful as positive allosteric GBR ($GABA_B$ receptor) modulators. A positive allosteric modulator of the $GABA_B$ receptor is defined as a compound which makes the $GABA_B$ receptor more sensitive to GABA and $GABA_B$ receptor agonists by binding to the $GABA_B$ receptor protein at a site different from that used by the endogenous ligand. The positive allosteric GBR modulator acts synergistically with an agonist and increases potency and/or intrinsic efficacy of the $GABA_B$ receptor agonist. It has also been shown that positive allosteric modulators acting at the $GABA_B$ receptor can produce an agonistic effect. Therefore, compounds of formula I can be effective as full or partial agonists.

A further aspect of the invention is a compound of the formula I for use in therapy.

As a consequence of the $GABA_B$ receptor becoming more sensitive to $GABA_B$ receptor agonists upon the administration of a positive allosteric modulator, an increased inhibition of transient lower esophageal sphincter relaxations (TLESR) for a $GABA_B$ agonist is observed. Consequently, the present invention is directed to the use of a positive allosteric $GABA_B$ receptor modulator according to formula I, optionally in combination with a $GABA_B$ receptor agonist, for the preparation of a medicament for the inhibition of transient lower esophageal sphincter relaxations (TLESRs).

A further aspect of the invention is the use of a compound of formula I, optionally in combination with a $GABA_B$ receptor agonist, for the manufacture of a medicament for the prevention of reflux.

Still a further aspect of the invention is the use of a compound of formula I, optionally in combination with a $GABA_B$ receptor agonist, for the manufacture of a medicament for the treatment of gastroesophageal reflux disease (GERD).

Effective management of regurgitation in infants would be an important way of preventing, as well as curing lung disease due to aspiration of regurgitated gastric contents, and for managing failure to thrive, inter alia due to excessive loss of ingested nutrient. Thus, a further aspect of the invention is the use of a compound of formula I, optionally in combination with a $GABA_B$ receptor agonist, for the manufacture of a medicament for the treatment of lung disease.

Another aspect of the invention is the use of a compound of formula I, optionally in combination with a $GABA_B$ receptor agonist, for the manufacture of a medicament for the management of failure to thrive.

Another aspect of the invention is the use of a compound of formula I, optionally in combination with a $GABA_B$ receptor agonist, for the manufacture of a medicament for the treatment or prevention of asthma, such as reflux-related asthma.

A further aspect of the invention is the use of a compound of formula I, optionally in combination with a $GABA_B$ receptor agonist, for the manufacture of a medicament for the treatment or prevention of laryngitis or chronic laryngitis.

A further aspect of the present invention is a method for the inhibition of transient lower esophageal sphincter relaxations (TLESRs), whereby a pharmaceutically and pharmacologically effective amount of a compound of formula I, optionally in combination with a $GABA_B$ receptor agonist, is administered to subject in need of such inhibition.

Another aspect of the invention is a method for the prevention of reflux, whereby a pharmaceutically and pharmacologically effective amount of a compound of formula I, optionally in combination with a $GABA_B$ receptor agonist, is administered to a subject in need of such prevention.

Still a further aspect of the invention is a method for the treatment of gastroesophageal reflux disease (GERD), whereby a pharmaceutically and pharmacologically effective amount of a compound of formula I, optionally in combination with a $GABA_B$ receptor agonist, is administered to a subject in need of such treatment.

Another aspect of the present invention is a method for the treatment or prevention of regurgitation, whereby a pharmaceutically and pharmacologically effective amount of a compound of formula I, optionally in combination with a $GABA_B$ receptor agonist, is administered to a subject in need of such treatment.

Yet another aspect of the invention is a method for the treatment or prevention of regurgitation in infants, whereby a pharmaceutically and pharmacologically effective amount of a compound of formula I, optionally in combination with a $GABA_B$ receptor agonist, is administered to a subject in need of such treatment.

Still a further aspect of the invention is a method for the treatment, prevention or inhibition of lung disease, whereby a pharmaceutically and pharmacologically effective amount of a compound of formula I, optionally in combination with a $GABA_B$ receptor agonist, is administered to a subject in need of such treatment. The lung disease to be treated may inter alia be due to aspiration of regurgitated gastric contents.

Still a further aspect of the invention is a method for the management of failure to thrive, whereby a pharmaceutically and pharmacologically effective amount of a compound of formula I, optionally in combination with a $GABA_B$ receptor agonist, is administered to a subject in need of such treatment.

A further aspect of the invention is a method for the treatment or prevention of asthma, such as reflux-related asthma, whereby a pharmaceutically and pharmacologically effective amount of a compound of formula I, optionally in combination with a $GABA_B$ receptor agonist, is administered to a subject in need of such treatment.

A further aspect of the invention is a method for the treatment or prevention of laryngitis or chronic laryngitis, whereby a pharmaceutically and pharmacologically effective amount of a compound of formula I, optionally in combination with a $GABA_B$ receptor agonist, is administered to a subject in need of such treatment.

A further embodiment is the use of a compound of formula I, optionally in combination with a $GABA_B$ receptor agonist, for the manufacture of a medicament for the treatment of a functional gastrointestinal disorder (FGD). Another aspect of the invention is a method for the treatment of a functional gastrointestinal disorder, whereby an effective amount of a compound of formula I, optionally in combination with a $GABA_B$ receptor agonist, is administered to a subject suffering from said condition.

A further embodiment is the use of a compound of formula I, optionally in combination with a $GABA_B$ receptor agonist, for the manufacture of a medicament for the treatment of functional dyspepsia. Another aspect of the invention is a method for the treatment of functional dyspepsia, whereby an effective amount of a compound of formula I, optionally in combination with a $GABA_B$ receptor agonist, is administered to a subject suffering from said condition.

Functional dyspepsia refers to pain or discomfort centered in the upper abdomen.

Discomfort may be characterized by or combined with upper abdominal fullness, early satiety, bloating or nausea. Etiologically, patients with functional dyspepsia can be divided into two groups:

1—Those with an identifiable pathophysiological or microbiologic abnormality of uncertain clinical relevance (e.g. *Helicobacter pylori* gastritis, histological duodenitis, gallstones, visceral hypersensitivity, gastroduodenal dysmotility)

2—Patients with no identifiable explanation for the symptoms.

Functional dyspepsia can be diagnosed according to the following:

At least 12 weeks, which need not be consecutive within the preceding 12 months of 1—Persistent or recurrent dyspepsia (pain or discomfort centered in the upper abdomen) and 2—No evidence of organic disease (including at upper endoscopy) that is likely to explain the symptoms and 3—No evidence that dyspepsia is exclusively relieved by defecation or associated with the onset of a change in stool frequency or form.

Functional dyspepsia can be divided into subsets based on distinctive symptom patterns, such as ulcer-like dyspepsia, dysmotility-like dyspepsia and unspecified (non-specific) dyspepsia.

Currently existing therapy of functional dyspepsia is largely empirical and directed towards relief of prominent symptoms. The most commonly used therapies still include antidepressants.

A further aspect of the invention is the use of a compound according to formula I, optionally in combination with a $GABA_B$ receptor agonist, for the manufacture of a medicament for the treatment or prevention of irritable bowel syndrome (IBS), such as constipation predominant IBS, diarrhea predominant IBS or alternating bowel movement predominant IBS.

A further aspect of the invention is a method for the treatment or prevention of irritable bowel syndrome (IBS), whereby a pharmaceutically and pharmacologically effective amount of a compound of formula I, optionally in combination with a $GABA_B$ receptor agonist, is administered to a subject in need of such treatment.

IBS is herein defined as a chronic functional disorder with specific symptoms that include continuous or recurrent abdominal pain and discomfort accompanied by altered bowel function, often with abdominal bloating and abdominal distension. It is generally divided into 3 subgroups according to the predominant bowel pattern:

1—diarrhea predominant

2—constipation predominant

3—alternating bowel movements.

Abdominal pain or discomfort is the hallmark of IBS and is present in the three subgroups. IBS symptoms have been categorized according to the Rome criteria and subsequently modified to the Rome II criteria. This conformity in describing the symptoms of IBS has helped to achieve consensus in designing and evaluating IBS clinical studies.

The Rome II diagnostic criteria are:
1—Presence of abdominal pain or discomfort for at least 12 weeks (not necessarily consecutively) out of the preceding year
2—Two or more of the following symptoms:
a) Relief with defecation
b) Onset associated with change in stool frequency
c) Onset associated with change in stool consistency A further aspect of the invention is the use of a compound according to formula I, optionally in combination with a $GABA_B$ receptor agonist, for the manufacture of a medicament for the treatment or prevention CNS disorders, such as anxiety.

A further aspect of the invention is a method for the treatment or prevention of CNS disorders, such as anxiety, whereby a pharmaceutically and pharmacologically effective amount of a compound of formula I, optionally in combination with a $GABA_B$ receptor agonist, is administered to a subject in need of such treatment.

A further aspect of the invention is the use of a compound according to formula I, optionally in combination with a $GABA_B$ receptor agonist, for the manufacture of a medicament for the treatment or prevention of depression.

A further aspect of the invention is a method for the treatment or prevention of depression, whereby a pharmaceutically and pharmacologically effective amount of a compound of formula I, optionally in combination with a $GABA_B$ receptor agonist, is administered to a subject in need of such treatment.

For the purpose of this invention, the term "agonist" should be understood as including full agonists as well as partial agonists, whereby a "partial agonist" should be understood as a compound capable of partially, but not fully, activating $GABA_B$ receptors.

The wording "TLESR", transient lower esophageal sphincter relaxations, is herein defined in accordance with Mittal, R. K., Holloway, R. H., Penagini, R., Blackshaw, L. A., Dent, J., 1995; *Transient lower esophageal sphincter relaxation. Gastroenterology* 109, pp. 601-610.

The wording "reflux" is defined as fluid from the stomach being able to pass into the esophagus, since the mechanical barrier is temporarily lost at such times.

The wording "GERD", gastroesophageal reflux disease, is defined in accordance with van Heerwarden, M. A., Smout A. J. P. M., 2000; *Diagnosis of reflux disease. Baillière's Clin. Gastroenterol.* 14, pp. 759-774.

A "combination" according to the invention may be present as a "fix combination" or as a "kit of parts combination".

A "fix combination" is defined as a combination wherein (i) a compound of formula I; and (ii) a $GABA_B$ receptor agonist are present in one unit. One example of a "fix combination" is a pharmaceutical composition wherein (i) a compound of formula I and (ii) a $GABA_B$ receptor agonist are present in admixture. Another example of a "fix combination" is a pharmaceutical composition wherein (i) a compound of formula I and (ii) a $GABA_B$ receptor agonist; are present in one unit without being in admixture.

A "kit of parts combination" is defined as a combination wherein (i) a compound of formula I and (ii) a $GABA_B$ receptor agonist are present in more than one unit. One example of a "kit of parts combination" is a combination wherein (i) a compound of formula I and (ii) a $GABA_B$ receptor agonist are present separately. The components of the "kit of parts combination" may be administered simultaneously, sequentially or separately, i.e. separately or together.

The term "positive allosteric modulator" is defined as a compound which makes a receptor more sensitive to receptor agonists by binding to the receptor protein at a site different from that used by the endogenous ligand.

The term "therapy" and the term "treatment" also include "prophylaxis" and/or prevention unless stated otherwise. The terms "therapeutic" and "therapeutically" should be construed accordingly.

Pharmaceutical Formulations

The compound of formula I can be formulated alone or in combination with a $GABA_B$ receptor agonist.

For clinical use, the compound of formula I, optionally in combination with a $GABA_B$ receptor agonist, is in accordance with the present invention suitably formulated into pharmaceutical formulations for oral administration. Also rectal, parenteral or any other route of administration may be contemplated to the skilled man in the art of formulations. Thus, the compound of formula I, optionally in combination with a $GABA_B$ receptor agonist, is formulated with a pharmaceutically and pharmacologically acceptable carrier or adjuvant. The carrier may be in the form of a solid, semi-solid or liquid diluent.

In the preparation of oral pharmaceutical formulations in accordance with the invention, the compound of formula I, optionally in combination with a $GABA_B$ receptor agonist, to be formulated is mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or compressed into tablets.

Soft gelatine capsules may be prepared with capsules containing a mixture of a compound of formula I, optionally in combination with a $GABA_B$ receptor agonist, with vegetable oil, fat, or other suitable vehicle for soft gelatine capsules. Hard gelatine capsules may contain a compound of formula I, optionally in combination with a $GABA_B$ receptor agonist, in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance(s) mixed with a neutral fat base; (ii) in the form of a gelatine rectal capsule which contains a compound of formula I, optionally in combination with a $GABA_B$ receptor agonist, in a mixture with a vegetable oil, paraffin oil, or other suitable vehicle for gelatine rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing a compound of formula I, optionally in combination with a $GABA_B$ receptor agonist, and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of formula I, optionally in combination with a GABA$_B$ receptor agonist, in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

In one aspect of the present invention, a compound of formula I, optionally in combination with a GABA$_B$ receptor agonist, may be administered once or twice daily, depending on the severity of the patient's condition. A typical daily dose of the compounds of formula I is from 0.1 to 100 mg per kg body weight of the subject to be treated, but this will depend on various factors such as the route of administration, the age and weight of the patient as well as of the severity of the patient's condition.

Methods of Preparation

The compounds according to formula I of the present invention, wherein $R^1$, $R^2$, $R^3$ and $R^4$ are each and independently defined as above, may be prepared by the following general method (Scheme 1; related literature: *Tetrahedron* (1982), 38:1435-1441).

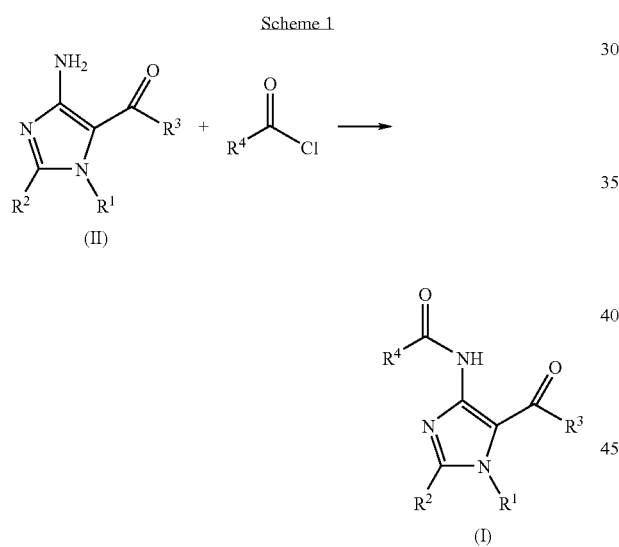

where aminoimidazoles (II) efficiently are acylated into (I), using acyl chlorides (typically 1.5-2.5 equivalents) in organic solvents such as THF or the like. The reaction is performed in the presence of polymer-supported diisopropylethylamine (PS-DIPEA; 1.5-3 equivalents) at ambient temperature to 50° C. with agitation over 4-18 hours. Filtration of the reaction mixture over the nucleophilic anion exchange resin Isolute-NH2, elution with THF and evaporation in vacuo yields the desired products as oils or amorphous solids.

The aminoimidazoles (II) are prepared from intermediates (III) or (IV) by heating the reagents under basic conditions with an alpha halo carbonyl compound (Scheme 2; literature: *Tetrahedron Lett.* (1966), 1885-1889 and *Monatshefte für Chemie* (1976), 107:1413-1421)

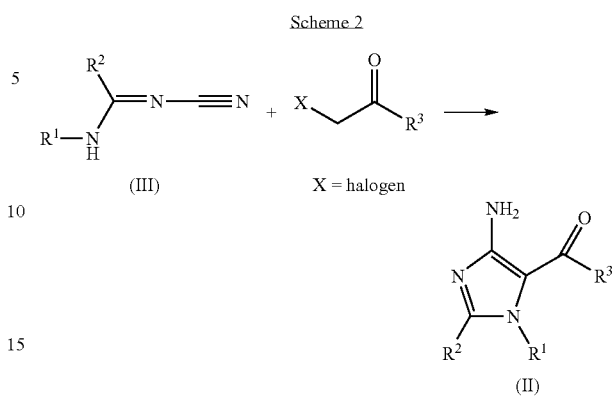

Intermediate (III), where $R^2$ is a $C_1$-$C_7$ alkoxy group, is prepared by substitution of the thiomethoxy group in intermediate (IV) by the corresponding $C_1$-$C_7$ alkoxy group according to Scheme 3.

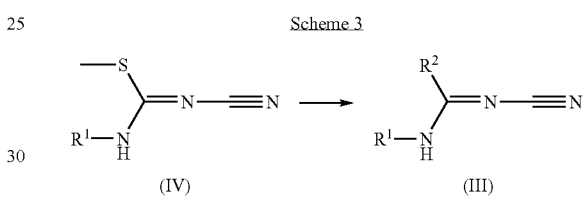

Intermediate (IV) is prepared by treating dimethylcyanodithioimidocarbonate in ethanol with 1-2 equivalent of the primary amine and reflux for 3-5 hours (see Scheme 4). The reaction mixture is allowed to cool, evaporated in vacuo and then the desired compounds are either collected by filtration directly or subsequently after the product has precipitated out by the addition of water.

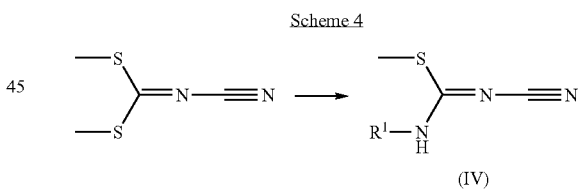

An alternative route to intermediate (II) consist of the treatment of intermediate (IV) with an alpha halo carbonyl compound in the presence of a base such as potassium carbonate providing intermediate (V). Subsequent treatment of intermediate (V) with nucleophiles such as e.g. alkoxy or thioalkoxy derivatives (e.g. NaOMe, NaOEt) provides intermediate (II) via thiomethyl group substitution and ring closure.

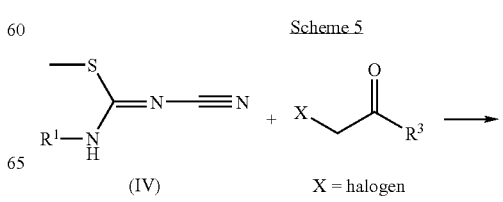

-continued

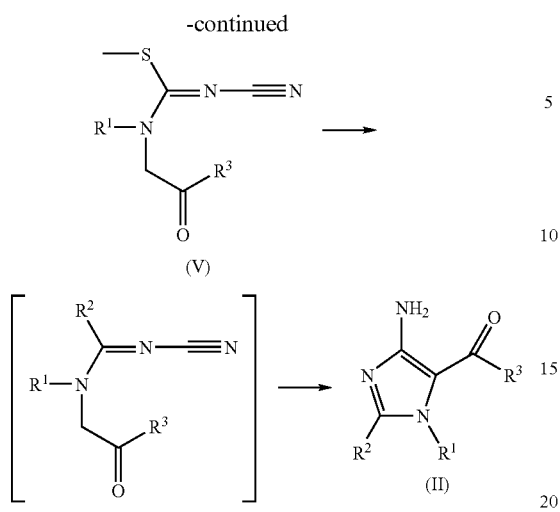

Furthermore, the intermediate (II) can be generated in an analogous way as described above by using diphenylcyanocarbonimidate as a starting material instead of dimethylcyanodithioimidocarbonate (Scheme 6; compare Bioorg. Med. Chem. Lett. 2001, 11, 2225-2228 and Bioorg. Med. Chem. Lett. 2004, 14, 4225-4229).

Scheme 6

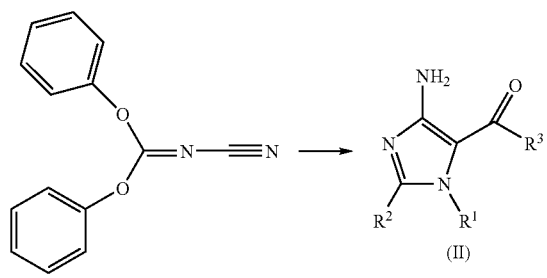

Multiple Parallel Synthesis of
4-acylamino-1H-imidazole-5-carboxylic acid ethyl esters Scheme 7

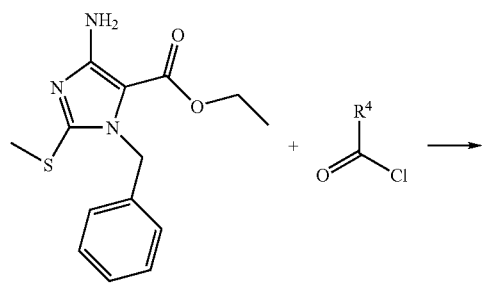

-continued

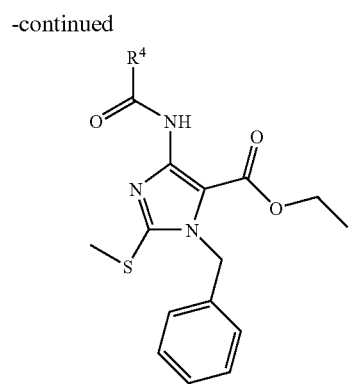

To 80 wells of a Robbins Flex Chem teflon 96 well block is added polymer-supported diisopropylethylamine (35 mg, 3.5 mmol/g) using a Titan Resin Loader™. To these 80 wells is subsequently added 1H-imidazole-5-carboxylic acid, 4-aniino-2-(methylthio)-1-(phenylmethyl)-, ethyl ester in THF (600 µl, 0.05 mmol) followed by 1 of 80 acyl chlorides (2-2.5 eq) dissolved in THF (600 µl). The block is sealed and rotated for 18h at room temperature, after which time each well is filtered over Isolute-NH2 (200 mg) eluting with THF (1.5 ml).

The THF is evaporated in vacuo to yield the acylated products as amorphous solids or oils.

Multiple Parallel Synthesis of
4-acylamino-1H-imidazole-5-carboxylic acid ethyl esters Scheme 8

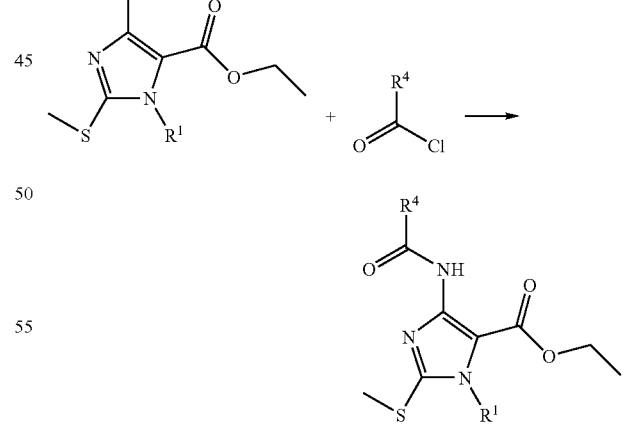

To 24 wells of a Robbins Flex Chem teflon 96 well block is added polymer-supported diisopropylethylamine (70 mg, 3.5 mmol/g) using a Titan Resin Loader™. To these wells is subsequently added 1 of 8 aminoimidazole per column in THF (600 µl, 0.1 mmol) followed by 1 of 3 acyl chlorides (2-2.5 eq) per row dissolved in THF (600 µl). The block is sealed and rotated for 18h at room temperature, after which time each well is faltered over Isolute-NH2 (400 mg) eluting with THF (2.5 ml).

EXAMPLES

Example 1

Synthesis of 1H-imidazole-5-carboxylic acid, 4-[(3,4-dichlorobenzoyl)amino]-2-(methylthio)-1-(phenylmethyl)-, ethyl ester

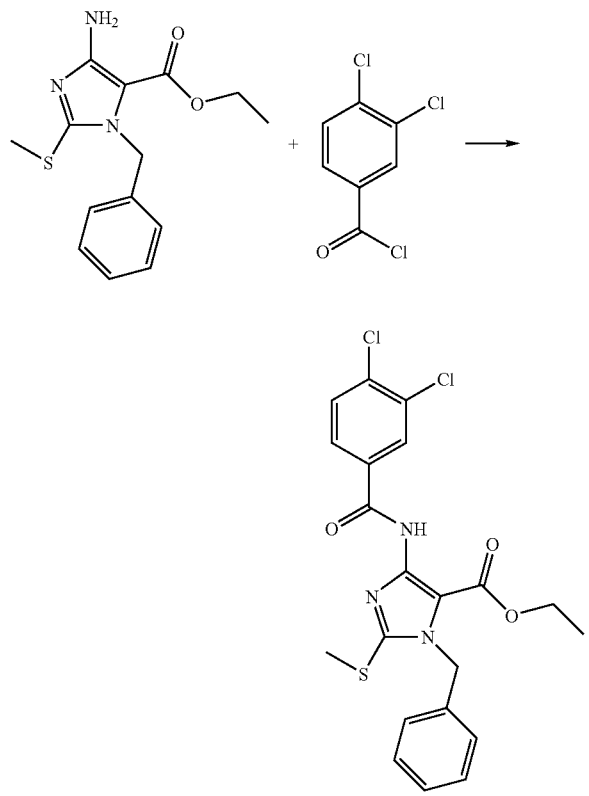

Scheme 9

1H-imidazole-5-carboxylic acid, 4-amino-2-(methylthio)-1-(phenylmethyl)-, ethyl ester (29 mg, 0.1 mmol) was dissolved in THF (700 µl) in a 1 ml vial. 50 mg of polymer supported diisopropylethylamine (3.5 mmol/g) and subsequently 3,4-dichlorobenzoyl chloride (31 mg, 0.15 mmol) was added. The reaction mixture was stirred overnight at room temperature and then filtered over an Isolute-NH2 column (200 mg) washing through with THF (1 ml). The THF was evaporated in vacuo to yield the product (35 mg, 75%).

NMR $^1$H 400 MHz (CDC13): 1.15 (3H, t, COOCH2C$\underline{H}$3), 2.85 (3H, s, SCH3), 4.3 (2H, q, COOC$\underline{H}$2CH3), 5.45 (2H, s, Ar—CH2), 7.1 (2H, Ar—H), 7.2-7.35 (3H, m, Ar—H), 7.55 (1H, Ar—H), 7.75 (1H, Ar—H), 8.05 (1H, Ar—H), 10.0 (1H, s, NH)

Example 2

Synthesis of 1H-imidazole-5-carboxylic acid, 4-amino-2-(methylthio)-1-(phenylmethyl)-, ethyl ester (Used as Intermediate)

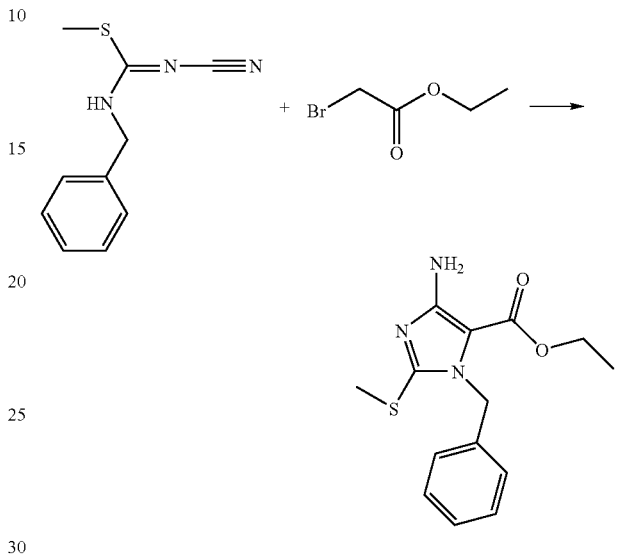

Scheme 10

Carbamimidothioic acid, N'-cyano-N-(phenylmethyl)-, methyl ester (2 g, 9.7 mmol), bromo ethyl acetate (1.79 g, 10.7 mmol) and potassium carbonate (1.48 g, 10.7 mmol) was dissolved/suspended in DMF (20 ml) and stirred for 1 h at 60° C. During the same time 0.56 g of sodium metal was dissolved in 12 ml of ethanol (99.9%). The reaction was cooled and the sodium ethoxide solution was added dropwise over 5 minutes. The reaction was then taken up to 90° C. for 5 minutes, cooled to room temperature and water added until precipitation of the product. The product was filtered and washed with ethanol/water (1:1) to yield 1.9 g (67%) of 1H-imidazole-5-carboxylic acid, 4-amino-2-(methylthio)-1-(phenylmethyl)-, ethyl ester. 0.5 g was recrystallised from ethanol/water to provide >95% pure (410 mg) 1H-imidazole-5-carboxylic acid, 4-amino-2-(methylthio)-1-(phenylmethyl)-, ethyl ester.

NMR $^1$H 400 MHz (CDC13): 1.15 (3H, t, COOCH2CH3), 2.60 (3H, s, SCH3), 4.25 (2H, q, COOCH2CH3), 4.95 (1H, br. s, NH2), 5.40 (2H, s, Ar—CH2), 7.1 (2H, Ar—H), 7.2-7.35 (3H, m, Ar—H)

Example 3

Synthesis of carbamimidothioic acid, N'-cyano-N-(phenylmethyl)-, methyl ester (Used as Intermediate)

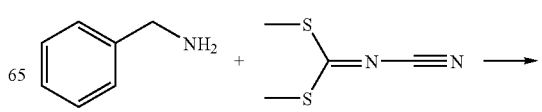

Scheme 11

-continued

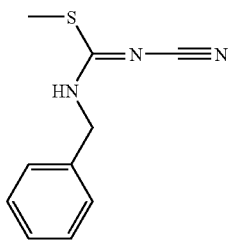

To dimethylcyanodithioimidocarbonate (8.2 g, 56 mmol) dissolved in ethanol (150 ml, 99.9%) was added benzylamine (10 g, 93 mmol). A thick white precipitate formed after about 10 seconds. The mixture was heated at reflux for 3 hours. The reaction was cooled to room temperature and the precipitate formed was collected by filtration and washed with ethanol (yield 6.43 g). The filtrate was evaporated and ethanol (50 ml) added. The resultant white precipitate was filtered, washed with ethanol to give a second crop (yield 2.66 g). Total yield of carbamimidothioic acid, N'-cyano-N-(phenylmethyl)-, methyl ester was 79%.

NMR $^1$H 400 MHz (DMSO): 2.6 (3H, s, SCH3), 4.5 (2H, s, Ar—CH2), 7.2-7.4 (5H, m, Ar—H), 8.9 (2H, br. s, NH2)

The following compounds were synthesized in an analogous method to Example 1 (RT=retention time, TOF ES+=electrospray MS, i.e. molecular weight+1):

| TOF ES+ | RT | Name | Structural formula |
|---|---|---|---|
| chloro: 416.16 (100%); 418.17 (33%) | 4.57 | 1H-imidazole-5-carboxylic acid, 4-[(4-chlorobenzoyl)amino]-2-(methylthio)-1-phenyl-, ethyl ester | |
| dichloro: 450.14 (100%); 452.13 (65%) | 4.91 | 1H-imidazole-5-carboxylic acid, 4-[(3,4-dichlorobenzoyl)amino]-2-(methylthio)-1-phenyl-, ethyl ester | |
| dichloro: 470.11 (100%); 472.1 (65%) | 5.01 | 1H-imidazole-5-carboxylic acid, 4-[(3,4-dichlorobenzoyl)amino]-2-(methylthio)-1-(2-thienylmethyl)-, ethyl ester | |

-continued

| TOF ES+ | RT | Name | Structural formula |
|---|---|---|---|
| bromo: 474.13 (100%); 476.13 (100%) | 4.79 | 1H-imidazole-5-carboxylic acid, 4-[(4-bromobenzoyl)amino]-2-(methylthio)-1-(phenylmethyl)-, ethyl ester | |
| chloro: 436.14 (100%); 438.14 (33%) | 4.69 | 1H-imidazole-5-carboxylic acid, 4-[(4-chlorobenzoyl)amino]-2-(methylthio)-1-(2-thienylmethyl)-, ethyl ester | |
| 438.3 | 5.06 | 1H-imidazole-5-carboxylic acid, 2-(methylthio)-4-[(1-oxo-2-phenylbutyl)amino]-1-(phenylmethyl)-, ethyl ester | |
| chloro: 430.18 (100%); 432.19 (33%) | 4.85 | 1H-imidazole-5-carboxylic acid, 4-[(4-chlorobenzoyl)amino]-2-(methylthio)-1-(phenylmethyl)-, ethyl ester | |
| 432.2 | 4.33 | 1H-imidazole-5-carboxylic acid, 4-[(4-methoxybenzoyl)amino]-2-(methylthio)-1-(2-thienylmethyl)-, ethyl ester | |

-continued

| TOF ES+ | RT | Name | Structural formula |
|---|---|---|---|
| 412.22 | 4.21 | 1H-imidazole-5-carboxylic acid, 4-[(4-methoxybenzoyl)amino]-2-(methylthio)-1-phenyl-, ethyl ester | |
| 452.27 | 5.37 | 1H-imidazole-5-carboxylic acid, 4-[[4-(1,1-dimethylethyl)benzoyl]amino]-2-(methylthio)-1-(phenylmethyl)-, ethyl ester | |
| dichloro: 464.14 (100%); 466.1 (65%) | 5.17 | 1H-imidazole-5-carboxylic acid, 4-[(3,4-dichlorobenzoyl)amino]-2-(methylthio)-1-(phenylmethyl)-, ethyl ester | |
| dichloro: 470.11 (100%); 472.11 (65%) | 5.01 | 1H-imidazole-5-carboxylic acid, 4-[(2,5-dichloro-3-thienyl)amino]-2-(methylthio)-1-(phenylmethyl)-, ethyl ester | |

-continued

| TOF ES+ | RT | Name | Structural formula |
|---|---|---|---|
| chloro: 410.21 (100%); 412.21 (33%) | 5.09 | 1H-imidazole-5-carboxylic acid, 4-[(4-chlorobenzoyl)amino]-1-(3-methylbutyl)-2-(methylthio)-, ethyl ester | |
| dichloro: 444.18 (100%); 446.1 (65%) | 5.41 | 1H-imidazole-5-carboxylic acid, 4-[(3,4-dichlorobenzoyl)amino]-1-(3-methylbutyl)-2-(methylthio)-, ethyl ester | |
| 440.28 | 4.93 | 1H-imidazole-5-carboxylic acid, 2-(methylthio)-4-[(1-oxo-2-phenoxypropyl)amino]-1-(phenylmethyl)-, ethyl ester | |
| 424.2 | 5.0 | 1H-imidazole-5-carboxylic acid, 2-(methylthio)-4-[(1-oxo-2-phenylbutyl)amino]-1-phenyl-, ethyl ester | |

-continued

| TOF ES+ | RT | Name | Structural formula |
|---|---|---|---|
| 508 | 4.88 | 1H-imidazole-5-carboxylic acid, 4-[(4-iodobenzoyl)amino]-2-(methylthio)-1-phenyl-, ethyl ester | |

| TOF ES+ | RT | Name | Structural formula |
|---|---|---|---|
| 406.26 | 4.74 | 1H-imidazole-5-carboxylic acid, 4-[(4-methoxybenzoyl)amino]-1-(3-methylbutyl)-2-(methylthio)-, ethyl ester | |
| chloro: 453.23 (100%); 455.23 (33%) | 3.68 | 1H-imidazole-5-carboxylic acid, 4-[(4-chlorobenzoyl)amino]-2-(methylthio)-1-[2-(4-morpholinyl)ethyl]-, ethyl ester | |
| dichloro: 487.20 (100%); 489.20 (65%) | 4.06 | 1H-imidazole-5-carboxylic acid, 4-[(3,4-dichlorobenzoyl)amino]-2-(methylthio)-1-[2-(4-morpholinyl)ethyl]-, ethyl ester | |

-continued

| TOF ES+ | RT | Name | Structural formula |
|---|---|---|---|
| 449.29 | | 1H-imidazole-5-carboxylic acid, 4-[(4-methoxybenzoyl)amino]-2-(methylthio)-1-[2-(4-morpholinyl)ethyl]-, ethyl ester | |
| trichloro: 498.12 (100%); 500.1 (100%); 502.12 (32%) | 5.41 | 1H-imidazole-5-carboxylic acid, 4-[(4-chlorobenzoyl)amino]-1-[(3,4-dichlorophenyl)methyl]-2-(methylthio)-, ethyl ester | |
| Cl4: 532.10 (100%); 534.09 (131%); 536.10 (64%) | 5.73 | 1H-imidazole-5-carboxylic acid, 4-[(3,4-dichlorobenzoyl)amino]-1-[(3,4-dichlorophenyl)methyl]-2-(methylthio)-, ethyl ester | |
| dichloro: 494.18 (100%); 496.1 (65%) | 5.07 | 1H-imidazole-5-carboxylic acid, 1-[(3,4-dichlorophenyl)methyl]-4-[(4-methoxybenzoyl)amino]-2-(methylthio)-, ethyl ester | |

-continued

| TOF ES+ | RT | Name | Structural formula |
|---|---|---|---|
| chloro:<br>460.16 (100%);<br>462.16 (33%) | 4.59 | 1H-imidazole-5-carboxylic acid, 1-(1,3-benzodioxol-5-yl)-4-[(4-chlorobenzoyl)amino]-2-(methylthio)-, ethyl ester | |
| dichloro:<br>494.13 (100%);<br>496.1 (65%) | 3.67 | 1H-imidazole-5-carboxylic acid, 1-(1,3-benzodioxol-5-yl)-4-[(3,4-dichlorobenzoyl)amino]-2-(methylthio)-, ethyl ester | |
| 456.23 | 4.25 | 1H-imidazole-5-carboxylic acid, 1-(1,3-benzodioxol-5-yl)-4-[(4-methoxybenzoyl)amino]-2-(methylthio)-, ethyl ester | |
| 426.24 | 4.50 | 1H-imidazole-5-carboxylic acid, 4-[(4-methoxybenzoyl)amino]-2-(methylthio)-1-(phenylmethyl)-, ethyl ester | |
| 410.2 | 4.69 | 1H-imidazole-5-carboxylic acid, 4-[(3-methylbenzoyl)amino]-2-(methylthio)-1-(phenylmethyl)-, ethyl ester | |

-continued

| TOF ES+ | RT | Name | Structural formula |
|---|---|---|---|
| bromo: 474.12 (100%); 476.11 (100%) | 4.76 | 1H-imidazole-5-carboxylic acid, 4-[(3-bromobenzoyl)amino]-2-(methylthio)-1-(phenylmethyl)-, ethyl ester | |
| 362.2 | 3.95 | 1H-imidazole-5-carboxylic acid, 4-[(2-methyl-1-oxopropyl)amino]-2-(methylthio)-1-(phenylmethyl)-, ethyl ester | |
| 468.22 | 4.7 | 1H-imidazole-5-carboxylic acid, 4-[[(acetyloxy)phenylacetyl]amino]-2-(methylthio)-1-(phenylmethyl)-, ethyl ester | |
| 376.22 | 4.36 | 1H-imidazole-5-carboxylic acid, 4-[(2,2-dimethyl-1-,oxopropyl)amino]-2-(methylthio)-1-(phenylmethyl)-, ethyl ester | |
| 416.18 | 4.38 | 1H-imidazole-5-carboxylic acid, 2-(methylthio)-1-(phenylmethyl)-4-[(2-thienylacetyl)amino]-, ethyl ester | |

-continued

| TOF ES+ | RT | Name | Structural formula |
|---|---|---|---|
| 364.19 | 3.75 | 1H-imidazole-5-carboxylic acid, 4-[(methoxyacetyl)amino]-2-(methylthio)-1-(phenylmethyl)-, ethyl ester | |
| 418.29 | 5.28 | 1H-imidazole-5-carboxylic acid, 4-[(2-ethyl-1-oxohexyl)amino]-2-(methylthio)-1-(phenylmethyl)-, ethyl ester | |
| 376.24 | 4.33 | 1H-imidazole-5-carboxylic acid, 2-(methylthio)-4-[(1-oxopentyl)amino]-1-(phenylmethyl)-, ethyl ester | |
| 477.24 | 4.74 | 1H-imidazole-5-carboxylic acid, 4-[[(5-methyl-3-phenyl-4-isoxazolyl)carbonyl]amino]-2-(methylthio)-1-(phenylmethyl)-, ethyl ester | |
| 505.23 | 4.84 | 1H-imidazole-5-carboxylic acid, 2-(methylthio)-1-(phenylmethyl)-4-[[[2-(phenylthio)-3-pyridinyl]carbonyl]amino]-, ethyl ester | |

-continued

| TOF ES+ | RT | Name | Structural formula |
|---|---|---|---|
| 388.24 | 4.46 | 1H-imidazole-5-carboxylic acid, 4-[(cyclopentylcarbonyl)amino]-2-(methylthio)-1-(phenylmethyl)-, ethyl ester | |
| 390.25 | 4.59 | 1H-imidazole-5-carboxylic acid, 4-[(2-methyl-1-oxopentyl)amino]-2-(methylthio)-1-(phenylmethyl)-, ethyl ester | |
| 410.24 | 4.6 | 1H-imidazole-5-carboxylic acid, 4-[(2-methylbenzoyl)amino]-2-(methylthio)-1-(phenylmethyl)-, ethyl ester | |
| 468.28 | 5.37 | 1H-imidazole-5-carboxylic acid, 4-[(4-butoxybenzoyl)amino]-2-(methylthio)-1-(phenylmethyl)-, ethyl ester | |
| 406.21 | 3.83 | 1H-imidazole-5-carboxylic acid, 4-[(4-methoxy-1,4-dioxobutyl)amino]-2-(methylthio)-1-(phenylmethyl)-, ethyl ester | |

-continued

| TOF ES+ | RT | Name | Structural formula |
|---|---|---|---|
| 374.22 | 4.31 | 1H-imidazole-5-carboxylic acid, 4-[(3-methyl-1-oxo-2-butenyl)amino]-2-(methylthio)-1-(phenylmethyl)-, ethyl ester | |
| chloro: 436.13 (100%); 438.14 (33%) | 4.76 | 1H-imidazole-5-carboxylic acid, 4-[[(3-chloro-2-thienyl)carbonyl]amino-2-(methylthio)-1-(phenylmethyl)-, ethyl ester | |
| 390.26 | 4.55 | 1H-imidazole-5-carboxylic acid, 4-[(3,3-dimethyl-1-oxobutyl)amino]-2-(methylthio)-1-(phenylmethyl)-, ethyl ester | |
| chloro: 499.24 (100%); 501.24 (33%) | 4.33 | 1H-imidazole-5-carboxylic acid, 4-[[(4-chloro-1,3-dimethyl-1H-pyrazolo[3,4-b]pyridin-5-yl)carbonyl]amino]-2-(methylthio)-1-(phenylmethyl)-, ethyl ester | |

-continued

| TOF ES+ | RT | Name | Structural formula |
|---|---|---|---|
| 482.3 | 5.68 | 1H-imidazole-5-carboxylic acid, 4-[[[4-(1,1-dimethylethyl)phenoxy]acetyl]amino]-2-(methylthio)-1-(phenylmethyl)-, ethyl ester | 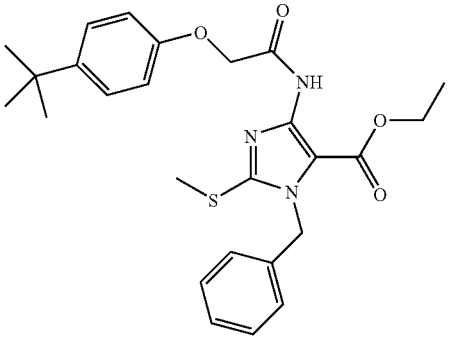 |
| 471.23 | 4.59 | 1H-imidazole-5-carboxylic acid, 2-(methylthio)-4-[[(2-nitrophenoxy)acetyl]amino]-1-(phenylmethyl)-, ethyl ester | 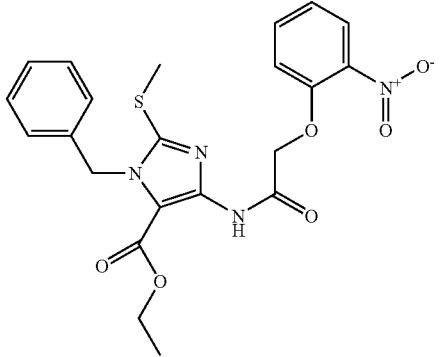 |
| 374.24 | 4.21 | 1H-imidazole-5-carboxylic acid, 2-(methylthio)-4-[(1-oxo-4-pentenyl)amino]-1-(phenylmethyl)-, ethyl ester | 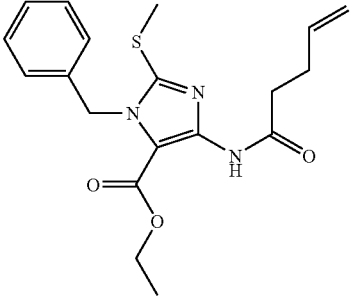 |
| 486.29 | 5.39 | 1H-imidazole-5-carboxylic acid, 4-[(diphenylacetyl)amino]-2-(methylthio)-1-(phenylmethyl)-, ethyl ester | 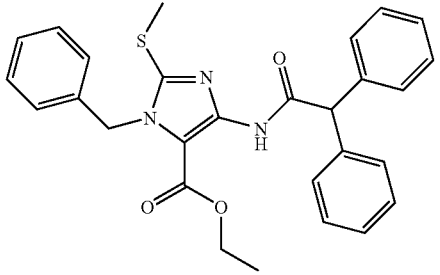 |

-continued

| TOF ES+ | RT | Name | Structural formula |
|---|---|---|---|
| 420.25 | 3.79 | 1H-imidazole-5-carboxylic acid, 4-[(5-methoxy-1,5-dioxopentyl)amino]-2-(methylthio)-1-(phenylmethyl)-, ethyl ester | 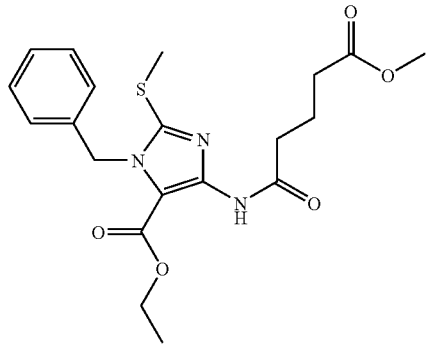 |
| 410.24 | 4.5 | 1H-imidazole-5-carboxylic acid, 2-(methylthio)-4-[(phenylacetyl)amino]-1-(phenylmethyl)-, ethyl ester | 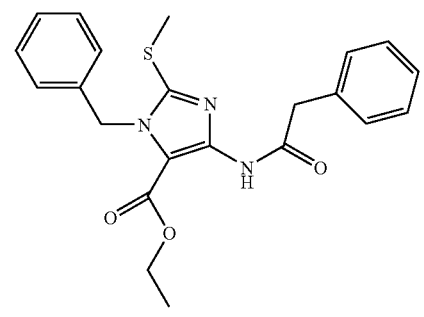 |
| 426.25 | 4.65 | 1H-imidazole-5-carboxylic acid, 4-[(2-methoxybenzoyl)amino]-2-(methylthio)-1-(phenylmethyl)-, ethyl ester | 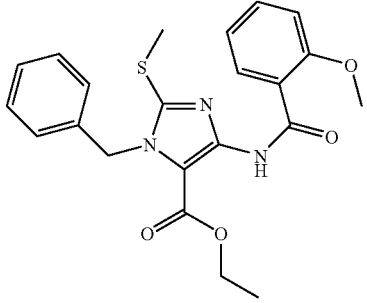 |
| 402.18 | 4.34 | 1H-imidazole-5-carboxylic acid, 2-(methylthio)-1-(phenylmethyl)-4-[(2-thienylcarbonyl)amino]-, ethyl ester | 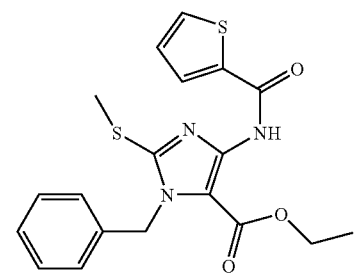 |
| chloro: 444.21 (100%); 446.21 (33%) | 4.81 | 1H-imidazole-5-carboxylic acid, 4-[[(4-chlorophenyl)acetyl]amino]-2-(methylthio)-1-(phenylmethyl)-, ethyl ester | 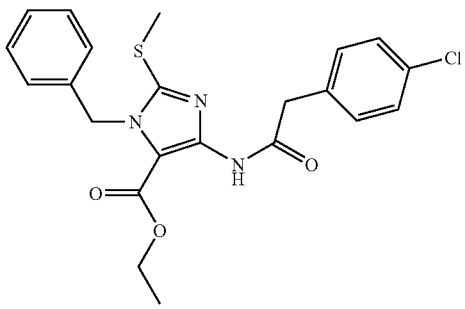 |

-continued

| TOF ES+ | RT | Name | Structural formula |
|---|---|---|---|
| 406.24 | 4.11 | 1H-imidazole-5-carboxylic acid, 4-[(3-ethoxy-1,3-dioxopropyl)amino]-2-(methylthio)-1-(phenylmethyl)-, ethyl ester | |
| 414.22 | 4.49 | 1H-imidazole-5-carboxylic acid, 4-[(4-fluorobenzoyl)amino]-2-(methylthio)-1-(phenylmethyl)-, ethyl ester | |
| chloro: 460.21 (100%); 462.22 (33%) | 5.11 | 1H-imidazole-5-carboxylic acid, 4-[[(4-chlorophenoxy)acetyl]amino]-2-(methylthio)-1-(phenylmethyl)-, ethyl ester | |
| 422.25 | 4.71 | 1H-imidazole-5-carboxylic acid, 2-(methylthio)-4-[[(2E)-1-oxo-3-phenyl-2-propenyl]amino]-1-(phenylmethyl)-, ethyl ester | |

| TOF ES+ | RT | Name | Structural formula |
|---|---|---|---|
| 440.28 | 4.93 | 1H-imidazole-5-carboxylic acid, 2-(methylthio)-4-[(1-oxo-2-phenoxypropyl)amino]-1-(phenylmethyl)-, ethyl ester | |
| 426.25 | 4.52 | 1H-imidazole-5-carboxylic acid, 4-[(3-methoxybenzoyl)amino]-2-(methylthio)-1-(phenylmethyl)-, ethyl ester | |
| 441.23 | 4.57 | 1H-imidazole-5-carboxylic acid, 2-(methylthio)-4-[(2-nitrobenzoyl)amino]-1-(phenylmethyl)-, ethyl ester | |
| 387.21 | 3.89 | 1H-imidazole-5-carboxylic acid, 4-[(5-isoxazolylcarbonyl)amino]-2-(methylthio)-1-(phenylmethyl)-, ethyl ester | |

| TOF ES+ | RT | Name | Structural formula |
|---|---|---|---|
| 440.24 | 4.36 | 1H-imidazole-5-carboxylic acid, 4-[(1,3-benzodioxol-5-ylcarbonyl)amino]-2-(methylthio)-1-(phenylmethyl)-, ethyl ester | |
| 414.23 | 4.53 | 1H-imidazole-5-carboxylic acid, 4-[(3-fluorobenzoyl)amino]-2-(methylthio)-1-(phenylmethyl)-, ethyl ester | |
| 415.25 | 4.03 | 1H-imidazole-5-carboxylic acid, 4-[[(3,5-dimethyl-4-isoxazolyl)carbonyl]amino]-2-(methylthio)-1-(phenylmethyl)-, ethyl ester | |
| 440.28 | 4.82 | 1H-imidazole-5-carboxylic acid, 2-(methylthio)-4-[[[(phenylmethoxy)acetyl]amino]-1-(phenylmethyl)-, ethyl ester | |

-continued

| TOF ES+ | RT | Name | Structural formula |
|---|---|---|---|
| 421.24 | 4.36 | 1H-imidazole-5-carboxylic acid, 4-[(4-cyanobenzoyl)amino]-2-(methylthio)-1-(phenylmethyl)-, ethyl ester | |
| 516.33 | 5.23 | 1H-imidazole-5-carboxylic acid, 2-(methylthio)-4-[[[4-(phenylmethoxy)phenyl]acetyl]amino]-1-(phenylmethyl)-, ethyl ester | |
| chloro: 430.21 (100%); 432.22 (33%) | 4.53 | 1H-imidazole-5-carboxylic acid, 4-[(2-chlorobenzoyl)amino]-2-(methylthio)-1-(phenylmethyl)-, ethyl ester | |
| chloro: 430.21 (100%); 432.21 (33%) | 4.81 | 1H-imidazole-5-carboxylic acid, 4-[(3-chlorobenzoyl)amino]-2-(methylthio)-1-(phenylmethyl)-, ethyl ester | |

| TOF ES+ | RT | Name | Structural formula |
| --- | --- | --- | --- |
| 416.31 | 5.01 | 1H-imidazole-5-carboxylic acid, 4-[(3-cyclopentyl-1-oxopropyl)amino]-2-(methylthio)-1-(phenylmethyl)-, ethyl ester | |
| 421.25 | 4.29 | 1H-imidazole-5-carboxylic acid, 4-[(3-cyanobenzoyl)amino]-2-(methylthio)-1-(phenylmethyl)-, ethyl ester | |
| dichloro: 464.19 (100%); 466.19 (65%) | 5.04 | 1H-imidazole-5-carboxylic acid, 4-[(2,4-dichlorobenzoyl)amino]-2-(methylthio)-1-(phenylmethyl)-, ethyl ester | |
| 426.27 | 4.7 | 1H-imidazole-5-carboxylic acid, 2-(methylthio)-4-[(phenoxyacetyl)amino]-1-(phenylmethyl)-, ethyl ester | |

-continued

| TOF ES+ | RT | Name | Structural formula |
|---|---|---|---|
| 452.23 | 5 | 1H-imidazole-5-carboxylic acid, 4-[(benzo[b]thien-2-ylcarbonyl)amino]-2-(methylthio)-1-(phenylmethyl)-, ethyl ester | |
| 334.21 | 3.4 | 1H-imidazole-5-carboxylic acid, 4-(acetylamino)-2-(methylthio)-1-(phenylmethyl)-, ethyl ester | |
| 396.25 | 4.28 | 1H-imidazole-5-carboxylic acid, 4-(benzoylamino)-2-(methylthio)-1-(phenylmethyl)-, ethyl ester | |
| chloro: 510.27 (100%); 512.28 (33%) | 5.66 | 1H-imidazole-5-carboxylic acid, 4-[[[5-(4-chlorophenyl)-2-methyl-3-furanyl]carbonyl]amino]-2-(methylthio)-1-(phenylmethyl)-, ethyl ester | |
| chloro: 488.28 (100%); 490.28 (33%) | 5.54 | 1H-imidazole-5-carboxylic acid, 4-[[2-(4-chlorophenoxy)-2-methyl-1-oxopropyl]amino]-2-(methylthio)-1-(phenylmethyl)-, ethyl ester | |

-continued

| TOF ES+ | RT | Name | Structural formula |
|---|---|---|---|
| 532.26 | 5.44 | 1H-imidazole-5-carboxylic acid, 4-[[3,5-bis(trifluoromethyl)benzoyl]amino]-2-(methylthio)-1-(phenylmethyl)-, ethyl ester | |
| 446.29 | 4.99 | 1H-imidazole-5-carboxylic acid, 2-(methylthio)-4-[(2-naphthalenylcarbonyl)amino]-1-(phenylmethyl)-, ethyl ester | |
| 418.1 | 4.67 | 1H-imidazole-5-carboxylic acid, 2-(methylthio)-1-phenyl 4-[(phenylsulfonyl)amino]-, ethyl ester | |
| 424.2 | 5 | 1H-imidazole-5-carboxylic acid, 2-(methylthio)-4-[(1-oxo-2-phenylbutyl)amino]-1-phenyl-, ethyl ester | |

| TOF ES+ | RT | Name | Structural formula |
|---|---|---|---|
| 458.2 | 5.22 | 1H-imidazole-5-carboxylic acid, 4-[([(1,1'-biphenyl]-4-ylcarbonyl)amino]-2-(methylthio)-1-phenyl-, ethyl ester | |
| 508 | 4.88 | 1H-imidazole-5-carboxylic acid, 4-[(4-iodobenzoyl)amino]-2-(methylthio)-1-phenyl-, ethyl ester | |
| 472.2 | 5.29 | 1H-imidazole-5-carboxylic acid, 4-[(diphenylacetyl)amino]-2-(methylthio)-1-phenyl-, ethyl ester | |

Intermediates:

Example 4

Methyl N-cyano-N'-phenylimidothiocarbamate

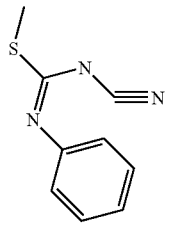

Aniline (0.093 mol) was added to a solution of dimethyl-cyanodithioimidocarbonate (0.146 mol) dissolved in 250 mL of ethanol(99.9%). The suspension was heated for 3 hours. The reaction was allowed to reach room temperature and the resulting precipitate was removed by filtration. The solid was washed with cool ethanol and dried under vacuum to afford the product.

$^1$H NMR (400 MHz, CDCl$_3$) δ 7.91 (s, 1H), 7.46-7.24 (m, 5H), 2.47 (s, 3H) MS m/z 192.05 (M+H)

Example 5

General Procedure for the 2-methylthio-substituted Intermediates (II)

All reactions were performed under inert gas atmosphere using dry glassware.

The corresponding bromoacetate (0.023 mol) was added dropwise to a suspension of methyl N-cyano-N'-phenylimidothiocarbamate (0.019 mol) and potassium carbonate (0.023 mol). The reaction mixture was heated at 85-90° C. for 2 h. After cooling to room temperature, 12 mL of a 4 M NaOH (0.048 mol) solution was added to the reaction mixture. The reaction was stopped after 15 min by addition of EtOAc. The organic phase was washed with brine, dried with NaSO$_4$, filtered and concentrated by evaporation. The crude product was purified by precipitation from EtOAc and a small amount heptane to afforded the desired product.

The following compounds were prepared according to example 5:

tert-butyl 4-amino-2-(methylthio)-1-phenyl-1H-imidazole-5-carboxylate

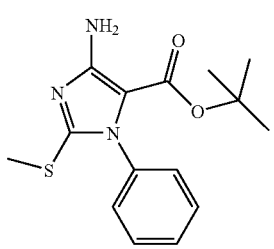

$^1$H NMR (400 MHz, CDCl$_3$) δ 7.46-7.38 (m, 3H), 7.25-7.20 (m, 2H), 4.99 (m, 2H), 2.57 (m, 3H) 1.21 (s, 9H) MS m/z (M+H)$^+$ tert-butyl 4-amino-2-(methylthio)-1-phenyl-1H-imidazole-5-carboxylate

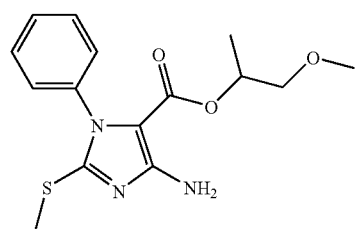

$^1$H NMR (400 MHz, CDCl$_3$) δ 8.02 (s, 1H), 7.49-7.39 (m, 3H), 7.3-7.22 (m, 2H), 5.12 (s, 2H) 5.07-4.98 (m, 1H), 3.25 (m, 3H), 3.20-3.08 (m, 2H) 2.96 (s, 3H), 2.88 (s, 3H), 2.56 (s, 3H), 1.07-1.01 (m, 3H) MS m/z 322.11 (M+H)$^+$

Cyclopentyl 4-amino-2-(methylthio)-1-phenyl-1H-imidazole-5-carboxylate

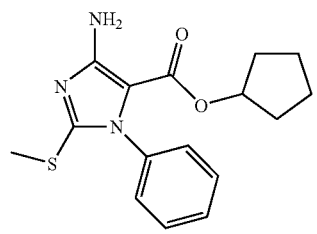

$^1$H NMR (400 MHz, CDCl$_3$) δ 7.46-7.38 (m, 3H), 7.24-7.16 (m, 2H), 5.15-5.08 (m, 1H), 5.07-4.97 (m, 2H) 2.53 (s, 3H), 1.69-1.53 (m, 2H), 1.44-1.17 (m, 6H) MS m/z 318.11 (M+H)$^+$

Isopropyl 4-amino-2-(methylthio)-1-phenyl-1H-imidazole-5-carboxylate

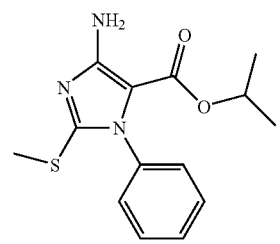

$^1$H NMR (400 MHz, CDCl$_3$) δ 7.45-7.37 (m, 3H), 7.25-7.19 (m, 2H), 5-03-4.88 (m, 3H), 2.53 (s, 3H) 0.97 (s, 6H) MS m/z 292.10 (M+H)$^+$

61

2,2-dimethylpropyl 4-amino-2-(methylthio)-1-phenyl-1H-imidazole-5-carboxylate

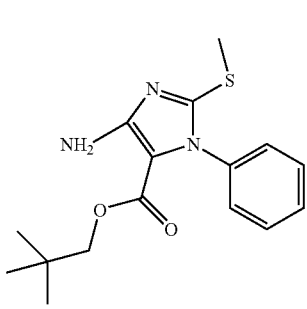

¹H NMR (400 MHz, CDCl₃) δ 7.47-7.36 (m, 3H), 7.28-7.20 (m, 2H), 5.10 (s, 2H), 3.70 (s, 2H) 2.53 (s, 3H),0.60 (s, 9H) MS m/z 320.05 (M+H)⁺

1-cyano-1-methylethyl 4-amino-2-(methylthio)-1-phenyl-1H-imidazole-5-carboxylate

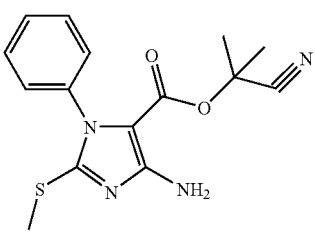

¹H NMR (400 MHz, CDCl₃) δ 7.46-7.38 (m, 3H), 7.26-7.18 (m, 2H), 5.17 (s, 2H), 1.37 (s, 6H) MS m/z 317.05 (M+H)⁺

1,1-dimethylpentyl 4-amino-2-(methylthio)-1-phenyl-1H-imidazole-5-carboxylate

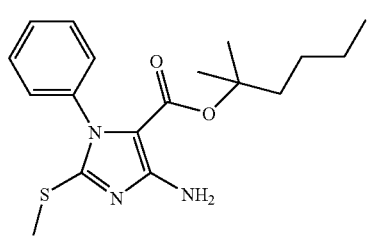

MS m/z 348.11 (M + H)⁺

62 tetrahydrofuran-3-yl 4-amino-2-(methylthio)-1-phenyl-1H-imidazole-5-carboxylate

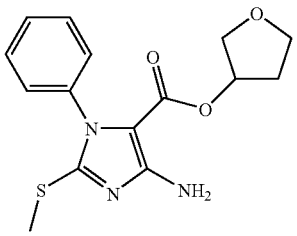

¹H NMR (400 MHz, CDCl₃) δ 7.46-7.39 (m, 3H), 7.26-7.17 (m, 2H), 5.24-5.05 (m, 1H), 5.05 (s, 2H) 3.81-3.74 (m, 1H), 3.70-3.62 (m, 1H), 3.51-3.44 (m, 1H), 3.41-3.28 (m, 1H) 2.54 (s, 31H), 1.96-1.86 (m, 1H), 1.66-1.51 (m, 1H) MS m/z 320.05 (M+H)⁺

2-methoxy-1,1-dimethylethyl 4-amino-2-(methylthio)-1-phenyl-1H-imidazole-5-carboxylate

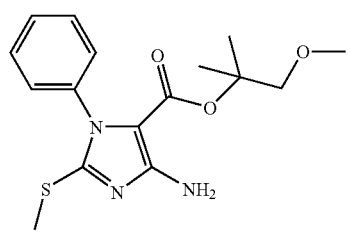

¹H NMR (400 MHz, CDCl₃) δ 7.48-7.42 (m, 3H), 7.29-7.25 (m, 2H), 5.07 (s, 2H), 3.31-3.22 (m, 5H) 2.56 (s, 3H), 1.30 (s, 6H) MS m/z 336.08 (M+H)⁺

1,1-dimethyl-2-oxopropyl 4-amino-2-(methylthio)-1-phenyl-1H-imidazole-5-carboxylate

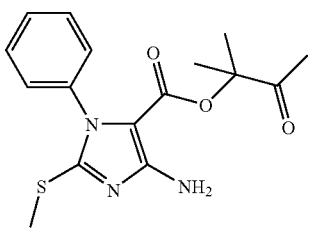

¹H NMR (400 MHz, CDCl₃) δ 7.51-7.48 (m, 3H), 7.32-7.26 (m, 2H), 5.14 (s, 2H), 2.58 (s, 3H) 2.05 (s, 3H), 1.15 (s, 6H) MS m/z 334.05 (M+H)⁺

1-(methoxymethyl)propyl 4-amino-2-(methylthio)-1-phenyl-1H-imidazole-5-carboxylate

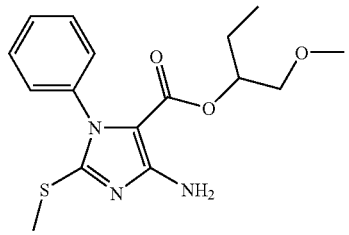

$^1$H NMR (400 MHz, CDCl$_3$) δ 7.43-7.38 (m, 3H), 7.29-7.19 (m, 2H), 5.05 (s, 2H), 4.93-4.84 (m, 1H) 3.22 (s, 3H), 3.26-3.08 (m, 2H), 2.53 (s, 3H), 1.51-1.37 (m, 1H) 1.34-1.16 (m, 1H), 0.74-0.66 (m, 3H) MS m/z 336.08 (M+H)$^+$

Example 6

General Procedure for the 2-methoxy-Substituted Intermediates (II)

All reactions were performed under inert gas atmosphere using dry glassware. The corresponding bromoacetate (0.014 mol) was added dropwise to a suspension of methyl N-cyano-N'-phenylimidothiocarbamate (0.012 mol) and potassium carbonate (0.014 mol) in 23 mL dry DMF. The reaction mixture was heated for 1.5 h. at 60 ° C. After cooling to room temperature, NaOMe (0.060 mol) dissolved in 30 mL dry MeOH was added slowly to get immediate transformation. After addition, the reaction was cooled in an icebath and water was added to get a precipitation which was filtered off and dried in vacuum. The crude was purified by high performance chromathography (MeCN:NH4OAc-buffert gradient 5:95-95:5%) to afford the desired product.

The following compound was prepared according to example 6:

2-methoxy-1,1-dimethylethyl 4-amino-2-methoxy-1-phenyl-1H-imidazole-5-carboxylate

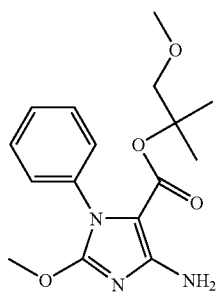

$^1$H NMR (400 MHz, CDCl$_3$) δ 7.41-7.29 (m, 3H), 7.26-7.19 (m, 2H), 5.07 (s, 2H), 3.93 (s, 3H) 3.27 (s, 5H), 1.29 (s, 6H) MS m/z 320.12 (M+H)$^+$

The following compounds were synthesized according to example 1 and analysed by NMR at 400 MHz:

tert-butyl 4-[(4-fluorobenzoyl)amino]-2-(methylthio)-1-phenyl-1H-imidazole-5-carboxylate

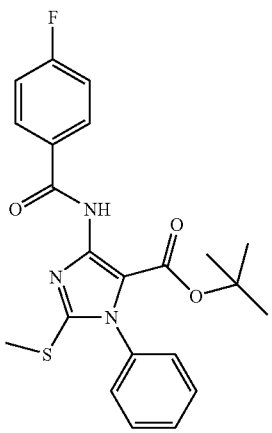

$^1$H NMR (400 MHz, CDCl$_3$) δ 10.12 (s, 1H), 8.02 (q, 2H), 7.48-7.46 (m, 3H), 7.26-7.23 (m, 2H), 7.17 (t, 2H), 2.7 (s, 3H), 1.16 (s, 9H) MS m/z 428.08 (M+H)$^+$ 2-methoxy-1-methylethyl 4-[(4-chlorobenzoyl)amino]-2-(methylthio)-1-phenyl-1H-imidazole-5-carboxylate

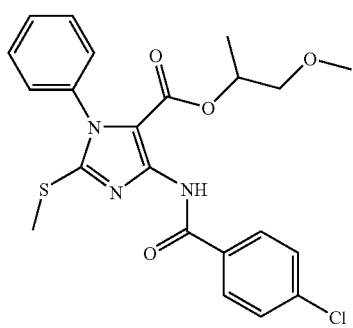

$^1$H NMR (400 MHz, CDCl$_3$) δ 10.01 (s, 1H), 7.94 (d, 2H), 7.49-7.42 (m, 5H), 7.28-7.22 (m, 2H), 5.12-5.02 (m, 1H), 3.17 (s, 3H), 3.13-3.07 (m, 1H), 2.99-2.91 (m, 1H), 2.69 (s, 3H), 0.98 (d, 3H) MS m/z 460.10 (M+H)$^+$

Cyclopentyl 4-[(4-chlorobenzoyl)amino]-2-(methylthio)-1-phenyl-1H-imidazole-5-carboxylate

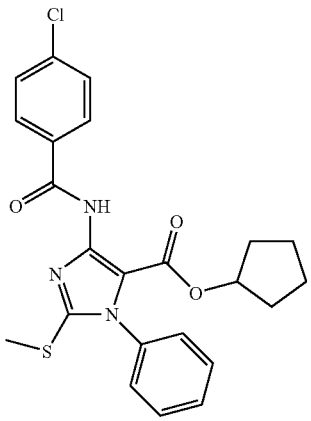

¹H NMR (400 MHz, CDCl₃) δ 10.17 (s, 1H), 7.93 (d, 2H), 7.51-7.41 (m, 5H), 7.27-7.20 (m, 2H), 5.18-5.12 (m, 1H), 2.69 (s, 3H), 1.66-1.54 (m, 2H), 1.4-1.24 (m, 4H), 1.2-1.07 (m, 2H) MS m/z 456.03 (M+H)⁺ tert-butyl 4-[(methoxyacetyl)amino]-2-(methylthio)-1-phenyl-1H-imidazole-5-carboxylate

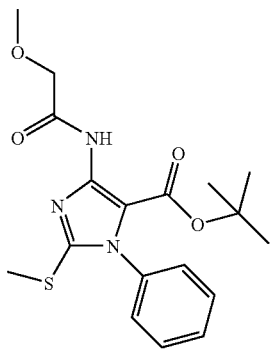

¹H NMR (400 MHz, CDCl₃) δ 9.85 (s, 1H), 7.50-7.42 (m, 3H), 7.27-7.20 (m, 2H), 4.09 (s, 2H), 3.52 (s, 3H), 2.65 (s, 3H), 1.23 (s, 9H) MS m/z 378.11 (M+H)⁺

Isopropyl 4-[(4-chlorobenzoyl)amino]-2-(methylthio)-1-phenyl-1H-imidazole-5-carboxylate

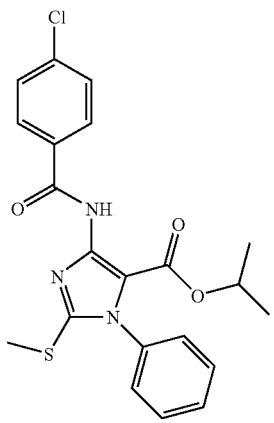

¹H NMR (400 MHz, CDCl₃) δ 10.09 (s, 1H), 7.92 (d, 2H), 7.48-7.41 (m, 5H), 7.26-7.20 (m, 2H), 4.98-4.88 (m, 1H), 2.68 (s, 3H), 0.91 (d, 6H) MS m/z 430.02 (M+H)⁺

2,2-dimethylpropyl 4-[(4-chlorobenzoyl)amino]-2-(methylthio)-1-phenyl-1H-imidazole-5-carboxylate

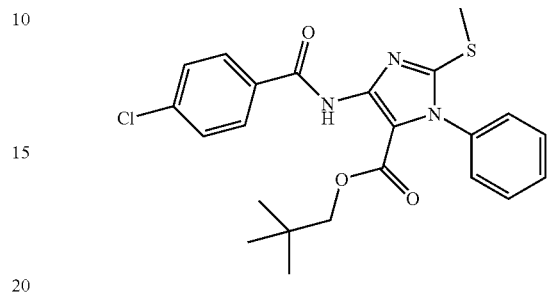

¹H NMR (400 MHz, CDCl₃) δ 10.32 (s, 1H), 7.93 (d, 2H), 7.52-7.42 (m, 5H), 7.30-7.25 (m, 2H), 3.73 (s, 2H), 2.69 (s, 3H), 0.52 (s, 9H) MS m/z 458.07 (M+H)⁺

1-cyano-1-methylethyl 4-[(4-chlorobenzoyl)amino]-2-(methylthio)-1-phenyl-1H-imidazole-5-carboxylate

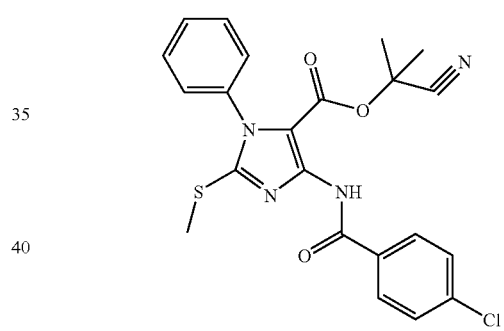

¹H NMR (400 MHz, CDCl₃) δ 9.93 (s, 1H), 7.93 (d, 2H), 7.51-7.44 (m, 5H), 7.28-7.22 (m, 2H), 2.7 (s, 3H), 1.35 (s, 6H) MS m/z 454.96 (M+H)⁺

1,1-dimethylpentyl 4-[(4-chlorobenzoyl)amino]-2-(methylthio)-1-phenyl-1H-imidazole-5-carboxylate

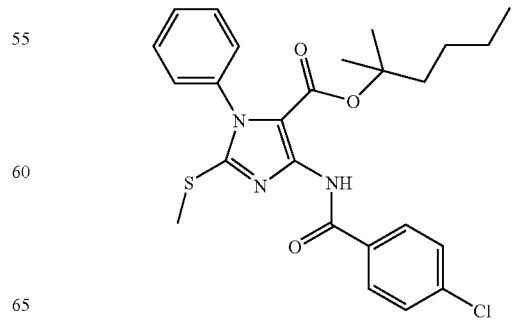

¹H NMR (400 MHz, CDCl₃) δ 10.07 (s, 1H), 7.93 (d, 2H), 7.48-7.42 (m, 5H), 7.26-7.20 (m, 2H), 2.67 (s, 3H), 1.46-1.39 (m, 2H), 1.16-1.05 (m, 8H), 0.95-0.85 (m, 2H), 0.8 (t, 3H) MS m/z 486.02 (M+H)⁺

Tetrahydrofuran-3-yl 4-[(4-chlorobenzoyl)amino]-2-(methylthio)-1-phenyl-1H-imidazole-5-carboxylate

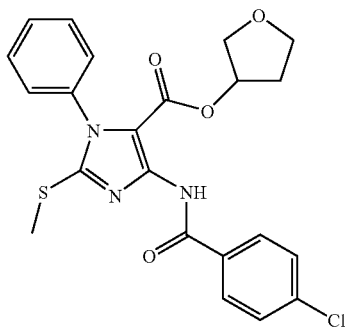

¹H NMR (400 MHz, CDCl₃) δ 10.02 (s, 1H), 7.92 (d, 2H), 7.51-7.43 (m, 5H), 7.28-7.22 (m, 2H), 5.27-5.22 (m, 1H), 3.77 (dd, 1H), 3.68-3.61 (m, 1H), 3.43 (d, 1H), 3.26 (q, 1H), 2.7 (s, 3H), 1.98-1.87 (m, 1H), 1.52-1.44 (m, 1H) MS m/z 320.05 (M+H)⁺

2-methoxy-1,1-dimethylethyl 4-[(4-chlorobenzoyl)amino]-2-(methylthio)-1-phenyl-1H-imidazole-5-carboxylate

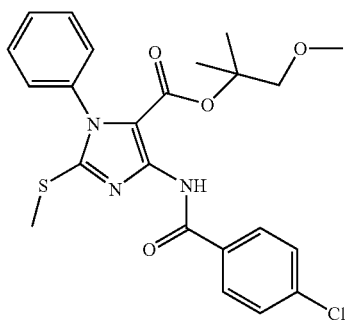

¹H NMR (400 MHz, CDCl₃) δ 9.99 (s, 1H), 7.91 (d, 2H), 7.49-7.42 (m, 5H), 7.27-7.21 (m, 2H), 3.20-3.13 (m, 5H), 2.66 (s, 3H), 1.18 (s, 6H) MS m/z 474.00 (M+H)⁺

1,1-dimethyl-2-oxopropyl 4-[(4-chlorobenzoyl)amino]-2-(methylthio)-1-phenyl-1H-imidazole-5-carboxylate

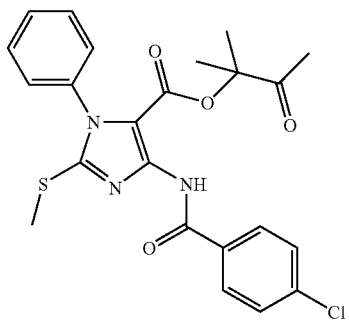

¹H NMR (400 MHz, CDCl₃) δ 9.96 (s, 1H), 7.89 (d, 2H), 7.53-7.42 (m, 5H), 7.33-7.25 (m, 2H), 2.7 (s, 3H), 2.01 (s, 3H), 1.09 (s, 6H) MS m/z 473.98 (M+H)⁺

1-(methoxymethyl)propyl 4-[(4-chlorobenzoyl)amino]-2-(methylthio)-1-phenyl-1H-imidazole-5-carboxylate

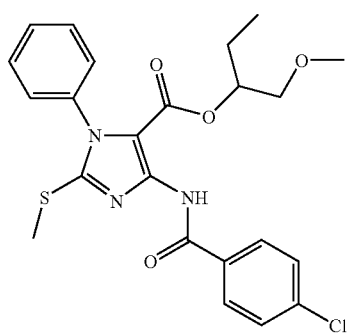

¹H NMR (400 MHz, CDCl₃) δ 10.06 (s, 1H), 7.93 (d, 2H), 7.49-7.40 (m, 5H), 7.28-7.22 (m, 2H) 5.01-4.92 (m, 1H), 3.21-3.13 (m, 4H), 3.02-2.96 (m, 1H), 2.69 (s, 3H), 1.47-1.13 (m, 2H), 0.66 (t, 3H) MS m/z 473.98 (M+H)⁺

2-methoxy-1,1-dimethylethyl 4-[(2,3-dihydro-1,4-benzodioxin-2-ylcarbonyl)amino]-2-methoxy-1-phenyl-1H-imidazole-5-carboxylate

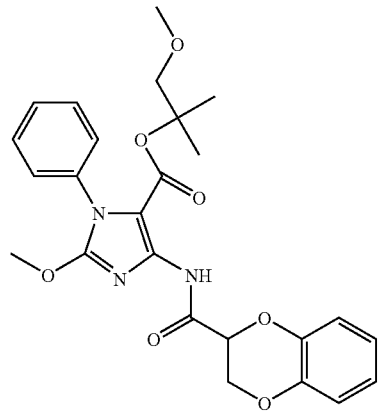

¹H NMR (500 MHz, CDCl₃) δ 11.57 (s, 1H), 8.73-8.66 (m, 3H), 8.51-8.47 (m, 2H), 8.39-8.35 (m, 1H), 8.21-8.15 (m, 3H), 6.12 (s, 1H), 5.94-5.90 (m, 1H), 5.63-5.58 (m, 1), 5.35 (s, 3H), 4.49 (d, 5H), 2.85 (s, 2H), 2.50 (d, 6H) MS m/z482.13 (M+H)⁺

2-methoxy-1,1-dimethylethyl 4-{[(3-chlorophenoxy)acetyl]amino}-2-methoxy-1-phenyl-1H-imidazole-5-carboxylate

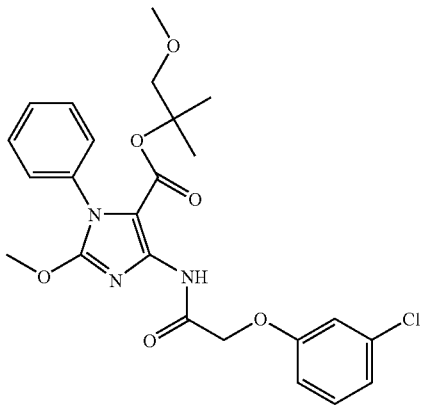

$^1$H NMR (400 MHz, CDCl$_3$) δ 10.25 (s, 1H), 7.46-7.36 (m, 3H), 7.29-7.17 (m, 3H), 7.07-6.95 (m, 2H), 6.93-6.35 (m, 1H), 4.64 (s, 2H), 4.06 (s, 3H), 3.21 (s, 5H), 1.20 (s, 6H) MS m/z 458.06 (M+H)$^+$

2-methoxy-1,1-dimethylethyl 4-[(4-chlorobenzoyl)amino]-2-methoxy-1-phenyl-1H-imidazole-5-carboxylate

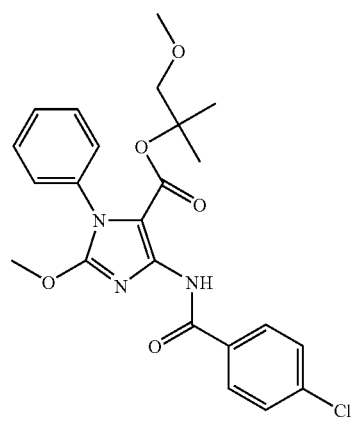

$^1$H NMR (400 MHz, CDCl$_3$) δ 10.12 (s, 1H), 7.91 (d, 2H), 7.47-7.36 (m, 5H), 7.25-7.20 (m, 2H), 4.09 (s, 3H), 3.19-3.13 (s, 5H), 1.20 (s, 6H) MS m/z 492.04 (M+H)$^+$

2-methoxy-1,1-dimethylethyl 4-[(2,4-dichlorobenzoyl)amino]-2-methoxy-1-phenyl-1H-imidazole-5-carboxylate

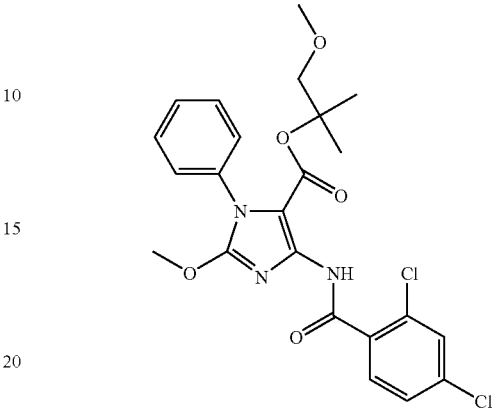

$^1$H NMR (400 MHz, CDCl$_3$) δ 9.72 (s, 1H), 7.69-7.56 (m, 1H), 7.47-7.36 (m, 4H), 7.35-7.28 (m, 1H) 7.26-7.18 (m, 2H), 4.19-3.95 (m, 3H), 3.24-2.96 (m, 5H) 1.23 (s, 6H) MS m/z 488.06 (M+H)$^+$

Analysis

LC-MS analysis was performed using a Micromass 8 probe MUX-LTC ESP+ system, purity being determined by single wavelength (254 nm) UV detection. Chromatography was performed over an Xterra™ MS C8 3.5 um, 4.6×30 mm column, 8 in parallel. The flow of 15 ml/min was split over the 8 columns to give a flow rate of 1.9 ml/min. The 10-minute chromatography gradient was as follows:

Mobile Phase A: 95% ACN+5% 0.010 M NH$_4$OAc
Mobile Phase B: 5% ACN+95% 0.010 M NH$_4$OAc

| 10 min | 0.0 min | 0% A |
|---|---|---|
| | 8.0 min | 100% A |
| | 9.0 min | 100% A |
| | 9.1 min | 0% A |

NMR analysis was performed at 400 MHz.

Biological Evaluation

Effects of the Positive Allosteric GABA$_B$ Receptor Modulator in a Functional In Vitro Assay.

The effect of GABA and baclofen on intracellular calcium release in CHO cells expressing the GABA$_{B(1A,2)}$ receptor heterodimer was studied in the presence or absence of the positive allosteric modulator. The positive allosteric modulator according to the invention increased both the potency and the efficacy of GABA.

The potency of the compounds i.e. the ability of the compounds to reduce the EC$_{50}$ of GABA was revealed by the concentration required to reduce GABA's EC$_{50}$ by 50%. These potencies were similar to the potency reported for CGP7930 (can be purchased from Tocris, Northpoint, Fourth Way, Avonmouth, Bristol, BS11 8TA, UK) by Urwyler et al. CGP7930 increases the potency of GABA from EC$_{50}$ of about 170-180 nM to EC$_{50}$ of about 35-50 nM.

Experimental Procedures

Materials

Nut mix F-12 (Ham) cell culture media, OPTI-MEM I reduced serum medium, Fetal bovine serum (FBS), penicillin/streptomycin solution (PEST), geneticin, HEPES (4-(2-hydroxyethyl)-1-piperazineethanesulfonic acid (buffer),1 M solution), Hank's Balanced Salt Solution (HBSS) and zeocin were from Life technologies (Paisley, Scotland); Polyethyleneimine, probenicid, baclofen and γ-aminobutyric acid (GABA) were from Sigma (St Louis, USA); Fluo-3 AM was from Molecular Probes (Oregon, USA). 4-Amino-n-[2,3-$^3$H] butyric acid ([$^3$H]GABA) was from Amersham Pharmacia Biotech (Uppsala, Sweden).

Generation of Cell Lines Expressing the GABA$_B$ Receptor

GABA$_B$R1a and GABA$_B$R2 were cloned from human brain cDNA and subcloned into pCI-Neo (Promega) and pALTER-1 (Promega), respectively. A GABA$_B$R1a-G$_{\alpha qi5}$ fusion protein expression vector was constructed using the pCI-Neo-GABA$_B$R1a cDNA plasmid and pLEC1-G$_{\alpha qi5}$ (Molecular Devices, CA). In order to make the G$_{\alpha qi5}$ pertussis toxin insensitive, Cys356 was mutated to Gly using standard PCR methodology with the primers 5'-GGATCCATGGCAT-GCTGCCTGAGCGA-3' (forward) and 5'-GCGGCCG CTCAGAAGAGGCCGCCGTCCTT-3' (reverse). The G$_{\alpha qi5mut}$ cDNA was ligated into the BamHI and NotI sites of pcDNA3.0 (Invitrogen). The GABA$_B$ R1a coding sequence was amplified by PCR from pCI-Neo-GABA$_B$R1a using the primers, 5'-GGATCCCCGGGGAGCCGGGCCC-3' (forward) and 5'-GGATCCCTTATAAAGCAAATGCACTCGA-3' (reverse) and subcloned into the BamHI site of pcDNA3.0-G$_{\alpha qi5mut}$.

In order to optimise the Kozak consensus sequence of GABA$_B$R2, in situ mutagenesis was performed using the Altered Sites Mutagenesis kit according to manufacturer's instruction (Promega) with the following primer, 5'-GAAT-TCGCACCATGGCTTCCC-3'. The optimised GABA$_B$R2 was then restricted from pALTER-1 with Xho I+Kpn I and subcloned into the mammalian expression vector pcDNA3.1 (−)/Zeo (Invitrogen) to produce the final construct, pcDNA3.1(−)/Zeo-GABA$_B$R2.

For generation of stable cell lines, CHO-K1 cells were grown in Nut mix F-12 (Ham) media supplemented with 10% FBS, 100 U/ml Penicillin and 100 μg/ml Streptomycin at 37° C. in a humidified CO$_2$-incubator. The cells were detached with 1 mM EDTA in PBS and 1 million cells were seeded in 100 mm petri dishes. After 24 hours the culture media was replaced with OptiMEM and incubated for 1 hour in a CO$_2$-incubator. For generation of a cell line expressing the GABA$_B$R1a/GABA$_B$R2 heterodimer, GABA$_B$R1a plasmid DNA (4 μg) GABA$_B$R2 plasmid DNA (4 μg) and lipofectamine (24 μl) were mixed in 5 ml OptiMEM and incubated for 45 minutes at room temperature. The cells were exposed to the transfection medium for 5 hours, which then was replaced with culture medium. The cells were cultured for an additional 10 days before selection agents (300 μg/ml hygromycin and 400 μg/ml geneticin) were added. Twenty-four days after transfection, single cell sorting into 96-well plates by flow cytometry was performed using a FACS Vantage SE (Becton Dickinson, Palo Alto, Calif.). After expansion, the GABA$_B$ receptor functional response was tested using the FLIPR assay described below. The clone with the highest functional response was collected, expanded and then subcloned by single cell sorting. The clonal cell line with the highest peak response in the FLIPR was used in the present study.

For generation of a stable cell line expressing GABA$_B$R1a-G$_{\alpha qi5}$ fusion protein and GABA$_B$R2, GABA$_B$R1a-G$_{\alpha qi5mut}$ plasmid DNA (8 μg) GABA$_B$R2 plasmid DNA (8 μg) and lipofectamine (24 μl) were mixed in 5 ml OptiMEM and incubated for 45 minutes at room temperature. The cells were exposed to the transfection medium for 5 hours, which then was replaced with culture medium. After forty-eight hours, the cells were detached and seeded in 6 well plates (2000 cells/well) and grown in culture medium supplemented with geneticin (400 μg/ml) and zeocin (250 μg/ml). After 4 days, cells from single colonies were collected and transferred to a 24-well plate. After 10 days, the cell clones were seeded in T-25 flasks and grown for another 16 days before they were tested for GABA$_B$ receptor mediated functional response. The clones that showed the highest peak response were collected and subcloned by seeding the cells in 6-well plates (1000 cells/well) and repeating the steps described above. The clonal cell line that gave the highest peak response in the FLIPR was used in the present study.

Measurement of GABA$_B$ Receptor Dependent Release of Intracellular Calcium in the FLIPR Measurement of GABA$_B$ receptor dependent release of intracellular calcium in the fluorescence imaging plate reader (FLIPR) was performed as described by Coward et al. *Anal. Biochem.* (1999) 270, 242-248, with some modifications. Transfected CHO cells were cultivated in Nut Mix F-12 (HAM) with Glutamax-I and supplemented with 10%, 100 U/ml penicillin and 100 μg/ml streptomycin, 250 μg/Ml zeocin and 400 μg/ml geneticin. Twenty-four hours prior to the experiment the cells (35,000 cells/well) were seeded in black-walled 96-well poly-D-lysine coated plates (Becton Dickinson, Bedford, UK) in culture medium without selection agents. The cell culture medium was aspirated and 100 μl of Fluo-3 loading solution (4 μM Fluo-3, 2.5 mM probenecid and 20 mM Hepes in Nut Mix F-12 (Ham)) was added. After incubation for 1 hour at 37° C. in a 5% CO$_2$ incubator, the dye-solution was aspirated and the cells were washed 2 times with 150 μl of wash solution (2.5 mM probenecid and 20 mM Hepes in HBSS) followed by addition of 150 μl of wash solution. The cells were then assayed in a fluorescence imaging plate reader (Molecular Devices Corp., CA, USA). Test compounds were diluted to 50 μM concentrations in HBSS containing 20 mM Hepes and 5% DMSO and added in a volume of 50 μl. The fluorescence was sampled every second for 60 s (10 s before and 50 s after the addition of test compound) before GABA (50 μl 7.6 nM-150 μM) was added and sampling continued every sixth second for additional 120 seconds.

GTPgS

[$^{35}$S]-GTPγS binding assays were performed at 30° C. for 45 min in membrane buffer (100 mM NaCl, 5 mM MgCl$_2$, 1 mM EDTA, 50 mM HEPES, pH 7.4) containing 0.025 μg/μl of membrane protein (prepared from the cell lines described above) with 0.01% bovine serum albumin (fatty acid free), 10 μM GDP, 100 μM DTT and 0.53 nM [$^{35}$S]-GTPγS (Amersham-Pharmacia Biotech) in a final volume of 200 μl. Non-specific binding was determined in the presence of 20 μM GTPγS. The reaction was started by the addition of GABA at concentration between 1 mM and 0.1 mM in the presence or absence of the required concentration of PAM. The reaction was terminated by addition of ice-cold wash buffer (50 mM Tris-HCl, 5 mM MgCl$_2$, 50 mM NaCl, pH 7.4) followed by rapid filtration under vacuum through Printed Filtermat A glass fiber filters (Wallac) (0.05% PEI treated) using a Micro 96 Harvester (Skatron Instruments). The filters were dried for 30 min at 50° C., then a paraffin scintillant pad was melted onto the filters and the bound radioactivity was determined using a 1450 Microbeta Trilux (Wallac) scintillation counter.

Calculations

GABA dose-response curves in the presence and absence of test compounds were constructed using the 4-parameter logistic equation, $y=y_{max}+((y_{min}-y_{max})/1+(x/C)^D)$ where $C=EC_{50}$ and D=slope factor.

The potency of PAM in GTPγS assays was determined by plotting the log $EC_{50}$ for GABA against the log concentration of the positive allosteric modulator in the presence of which the measurement was performed.

Generally, the potency of the compounds of formula I ranges from $EC_{50}$s between 20 μM and 0.001 μM. Examples of individual $EC_{50}$ values:

| Compound | $EC_{50}$ |
|---|---|
| 1H-imidazole-5-carboxylic acid, 4-[(3,4-dichlorobenzoyl)amino]-2-(methylthio)-1-(phenylmethyl)-, ethyl ester | 2.3 μM |
| 1H-imidazole-5-carboxylic acid, 2-(methylthio)-4-[(1-oxo-2-phenylbutyl)amino]-1-phenyl-, ethyl ester | 0.6 μM |
| 1,1-dimethylpentyl 4-[(4-chlorobenzoyl)amino]-2-(methylthio)-1-phenyl-1H-imidazole-5-carboxylate | 0.3 μM |
| 2-methoxy-1,1-dimethylethyl 4-[(2,3-dihydro-1,4-benzodioxin-2-ylcarbonyl)amino]-2-methoxy-1-phenyl-1H-imidazole-5-carboxylate | 0.3 μM |

Effect of Compounds in IBS Model (Colorectal Distension)

Colorectal Distension (CRD)

For CRD, a 3 cm polyethylene balloon with a connecting catheter (made in-house) was inserted in the distal colon, 2 cm from the base of the balloon to the anus, during light isoflurane anaesthesia (Forene®, Abbott Scandinavia AB, Sweden). The catheter was fixed to the base of the tail with tape. At the same time, an intravenous catheter (Neoflon®, Becton Dickinson AB, Sweden) was inserted in a tail vein for compounds administration. Thereafter, rats were placed in Bollman cages and allowed to recover from sedation for at least 15 min before starting the experiments.

During the CRD procedure, the balloons were connected to pressure transducers (P-602, CFM-k33, 100 mmHg; Bronkhorst Hi-Tec, Veenendal, The Netherlands). A customized barostat (AstraZeneca, Mölndal, Sweden) was used to control the air inflation and intraballoon pressure. A customized computer software (PharmLab on-line 4.0.1) running on a standard PC was used to control the barostat and to perform data collection and storage. The distension paradigm generated by the barostat were achieved by generating pulse patterns on an analog output channel. The CRD paradigms used consisted on repeated phasic distensions, 12 times at 80 mmHg, with a pulse duration of 30 s at 5 min intervals.

Responses to CRD were assessed by recording and quantitation of phasic changes in intraballoon pressure during the distending pulses. Pressure oscillations during the isobaric inflation of the intracolonic balloon reflect abdominal muscle contractions associated to the distension procedure and, therefore, are considered a valid assessment of the visceromotor response (VMR) associated to the presence of pain of visceral origin.

Data Collection and Analysis

The balloon pressure signals were sampled at 50 Hz and afterwards subjected to digital filtering. A highpass filter at 1 Hz was used to separate the contraction-induced pressure changes from the slow varying pressure generated by the barostat. A resistance in the airflow between the pressure generator and the pressure transducer further enhanced the pressure variations induced by abdominal contractions of the animal. In addition, a band-stop filtere at 49-51 Hz was used to remove line frequency interference. A customized computer software (PharmLab off-line 4.0.1) was used to quantify the phasic changes of the balloon pressure signals. The average rectified value (ARV) of the balloon pressure signals was calculated for the 30 s period before the pulse (baseline activity) and for the duration of the pulse (as a measure of the VMR to distension). When performing pulses analysis, the first and last second of each pulse were excluded since they reflect artefact signals produced by the barostat during inflation and deflation of the balloon and do not originate from the animal.

Results

The effect of the positive allosteric modulators was examined on the VMR to isobaric CRD in rats. A paradigm consisting of 12 distensions at 80 mmHg was used. The compounds were administered at a dose of 1 to 50 μmol/kg and VMR responses to CRD compared to the vehicle control. The compounds were effective reducing the VMR to CRD (at least a 20% inhibition compared to the vehicle used).

The invention claimed is:

1. A compound of the general formula I,

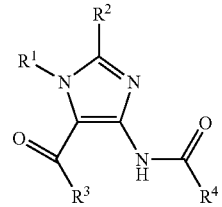

(I)

wherein:
R$^1$ is selected from the group consisting of:
(a) $C_1$-$C_{10}$ alkyl, $C_2$-$C_{10}$ alkenyl, $C_2$-$C_{10}$ alkynyl, and $C_3$-$C_{10}$ cycloalkyl, and is unsubstituted or substituted by:
(i) one or more substituents selected from the group consisting of $C_1$-$C_{10}$ alkoxy, $C_3$-$C_{10}$ cycloalkyl, $C_1$-$C_{10}$ thioalkoxy, halogen, hydroxy, mercapto, carboxylic acid, carboxylic acid ester, carboxylic acid amide, and nitrile, or
(ii) one or two aryl or heteroaryl groups; and
(b) aryl and heteroaryl, each of which is independently unsubstituted or substituted by:
(i) one or more substituents selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, and nitrile, or
(ii) one or two aryl or heteroaryl groups;
R$^2$ is $C_1$-$C_{10}$ alkoxy or $C_1$-$C_{10}$ thioalkoxy, and is unsubstituted or substituted by:
(a) one or more substituents selected from the group consisting of $C_1$-$C_{10}$ thioalkoxy, halogen, hydroxy, mercapto, carboxylic acid, carboxylic acid ester, carboxylic acid amide, and nitrile; or
(b) one or two aryl or heteroaryl groups;
R$^3$ is selected from the group consisting of:
(a) $C_1$-$C_{10}$ alkoxy, which is unsubstituted or substituted by:
(i) one or more substituents selected from the group consisting of $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, and nitrile, or
(ii) one or two aryl or heteroaryl groups;
(b) $C_1$-$C_{10}$ alkyl, $C_2$-$C_{10}$ alkenyl, $C_2$-$C_{10}$ alkynyl, and $C_3$-$C_{10}$ cycloalkyl, which is unsubstituted or substituted by:

(i) one or more substituents selected from the group consisting of $C_1$-$C_{10}$ alkoxy, $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, and nitrile, or (ii) one or two aryl or heteroaryl groups;

(c) aryl and heteroaryl, each of which is unsubstituted or substituted by:

(i) one or more substituents selected the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, and nitrile, or (ii) one or two aryl or heteroaryl groups; and (d) amino, which is unsubstituted or mono- or disubstituted with substituents independently selected from the group consisting of $C_1$-$C_{10}$ alkyl, $C_2$-$C_{10}$ alkenyl, $C_2$-$C_{10}$ alkynyl, and $C_3$-$C_{10}$ cycloalkyl;

$R^4$ is selected from the group consisting of:

(a) $C_1$-$C_{10}$ alkyl, $C_2$-$C_{10}$ alkynyl, $C_1$-$C_{10}$ alkoxy, and $C_3$-$C_{10}$ cycloalkyl, and is unsubstituted or substituted by:

(i) one or more substituents independently selected from the group consisting of $C_1$-$C_{10}$ alkoxy, $C_3$-$C_{10}$ cycloalkyl, $C_1$-$C_{10}$ thioalkoxy, halogen, hydroxy, mercapto, carboxylic acid, carboxylic acid ester, carboxylic acid amide, and nitrile, or (ii) one or two aryl or heteroaryl groups;

(b) aryl and heteroaryl, each of which is unsubstituted or substituted by:

(i) one or more substituents independently selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, and nitrile, or (ii) one or two aryl or heteroaryl groups;

wherein any of the alkyl, alkenyl, alkynyl and cycloalkyl substituents of $R^1$-$R^4$ may independently have one or more carbon atom(s) substituted by O, N or S;

with the proviso that the compound of formula I is not:

1H-imidazole-5-carboxylic acid, 4-(acetylamino)-1-methyl-2-(methylthio)-, ethyl ester;

1H-imidazole-5-carboxylic acid, 4-(acetylamino)-2-(methylthio)-1-phenyl-, ethyl ester;

1H-imidazole-5-carboxylic acid, 4-[(4-chlorobenzoyl)amino]-1-(2-furanylmethyl)-2-(methylthio)-, ethyl ester;

1H-imidazole-5-carboxylic acid, 4-(acetylamino)-1-(2-furanylmethyl)-2-(methylthio)-, ethyl ester;

1H-imidazole-5-carboxylic acid, 4-(acetylamino)-2-(methylthio)-1-(2-thienylmethyl)-, ethyl ester;

1H-imidazole-5-carboxylic acid, 2-(methylthio)-4-[[(5-nitro-2-furanyl)carbonyl]amino]-1-(2-thienylmethyl)-, ethyl ester;

1H-imidazole-5-carboxylic acid, 4-[[4-(1,1-dimethylethyl)benzoyl]amino]-1-(2-methoxyphenyl)-2-(methylthio)-, ethyl ester;

1H-imidazole-5-carboxylic acid, 4-[(2,4-dichlorobenzoyl)amino]-1-[4-(1-methylethyl)phenyl]-2-(methylthio)-, ethyl ester;

1H-imidazole-5-carboxylic acid, 1-[4-(1-methylethyl)phenyl]-4-[(2-methyl-1-oxopropyl)amino]-2-(methylthio)-, ethyl ester;

1H-imidazole-5-carboxylic acid, 1-[2-thienylmethyl]-4-[(chloro-acetyl)amino]-2-(methylthio)-, ethyl ester;

1H-imidazole-5-carboxylic acid, 1-[2-thienylmethyl]-4-[(dichloro-acetyl)amino]-2-(methylthio)-, ethyl ester; or 1H-imidazole-5-carboxylic acid, 1-[2-methoxyphenyl]-4-[(trichloro-acetyl)amino]-2-(methylthio)-, ethyl ester.

2. The compound according to claim 1, wherein $R^2$ is $C_1$-$C_{10}$ alkoxy which is unsubstituted or substituted by:

(a) one or more substituents selected from the group consisting of $C_1$-$C_{10}$ thioalkoxy, halogen, hydroxy, mercapto, carboxylic acid, carboxylic acid ester, carboxylic acid amide, and nitrile, or (b) one or two aryl or heteroaryl groups.

3. The compound according to claim 2, wherein $R^2$ is $C_1$-$C_5$ alkoxy which is unsubstituted or substituted by:

(a) one or more substituents selected from the group consisting of $C_1$-$C_{10}$ thioalkoxy, halogen, hydroxy, mercapto, carboxylic acid, carboxylic acid ester, carboxylic acid amide, and nitrile, or (b) one or two aryl or heteroaryl groups.

4. The compound according to claim 1, wherein $R^2$ represents $C_1$-$C_{10}$ thioalkoxy which is unsubstituted or substituted by:

(a) one or more substituents selected from the group consisting of $C_1$-$C_{10}$ thioalkoxy, halogen, hydroxy, mercapto, carboxylic acid, carboxylic acid ester, carboxylic acid amide, and nitrile, or (b) one or two aryl or heteroaryl groups.

5. The compound according to claim 4, wherein $R^2$ represents $C_1$-$C_5$ thioalkoxy which is unsubstituted or substituted by:

(a) one or more substituents selected from the group consisting of $C_1$-$C_{10}$ thioalkoxy, halogen, hydroxy, mercapto, carboxylic acid, carboxylic acid ester, carboxylic acid amide, and nitrile, or (b) one or two aryl or heteroaryl groups.

6. The compound according to claim 1, wherein $R^1$ is selected from the group consisting of:

(a) $C_1$-$C_7$ alkyl and $C_3$-$C_7$ cycloalkyl, and is unsubstituted or substituted by:

(i) one or more substituents selected from the group consisting of: $C_1$-$C_7$ alkoxy, $C_3$-$C_{10}$ cycloalkyl, hydroxy, carboxylic acid, carboxylic acid ester, carboxylic acid amide, and nitrile, (ii) one aryl or heteroaryl group; and (b) aryl and heteroaryl, each of which is independently unsubstituted or substituted by:

(i) one or more substituents selected from the group consisting of $C_1$-$C_7$ alkyl, $C_2$-$C_7$ alkenyl, $C_2$-$C_7$ alkynyl, $C_3$-$C_7$ cycloalkyl, $C_1$-$C_7$ alkoxy, $C_1$-$C_7$ thioalkoxy, halogen, hydroxy, mercapto, nitro, keto, carboxylic acid, carboxylic acid ester, carboxylic acid amide, and nitrile, or (ii) one or two aryl or heteroaryl groups.

7. The compound according to claim 6, wherein $R^1$ is $C_1$-$C_4$ alkyl which is unsubstituted or substituted by one or two aryl or heteroaryl groups.

8. The compound according to claim 1, wherein $R^3$ is $C_1$-$C_7$ alkoxy, and is unsubstituted or substituted by:

(a) one or more substituents selected from the group consisting of $C_1$-$C_{10}$ thioalkoxy, keto, $C_3$-$C_{10}$ cycloalkyl, halogen, hydroxy, mercapto, carboxylic acid, carboxylic acid ester, carboxylic acid amide and nitrile, or (b) one or two aryl or heteroaryl groups.

9. The compound according to claim 1, wherein $R^3$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, and is unsubstituted or substituted by:
   (a) one or more substituents selected from the group consisting of $C_1$-$C_{10}$ alkoxy, $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, and nitrile, or
   (ii) one or two aryl or heteroaryl groups.

10. The compound according claim 9, wherein $R^3$ is $C_1$-$C_{10}$ alkyl, and is unsubstituted or substituted by:
   (i) one or more substituents selected from the group consisting of $C_1$-$C_{10}$ alkoxy, $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, and nitrile, or
   (ii) one or two aryl or heteroaryl groups.

11. The compound according to claim 1, wherein $R^4$ is selected from the group consisting of $C_1$-$C_7$ alkyl, $C_2$-$C_7$ alkenyl, $C_2$-$C_7$ alkynyl and $C_3$-$C_7$ cycloalkyl, and is unsubstituted or substituted by:
   (a) one or more substituents selected from the group consisting of $C_1$-$C_7$ alkoxy, $C_1$-$C_7$ thioalkoxy, halogen, hydroxy, mercapto, carboxylic acid, carboxylic acid ester, carboxylic acid amide and nitrile, or
   (b) one or two aryl or heteroaryl groups.

12. The compound according to claim 1, wherein $R^4$ is aryl or heteroaryl, each of which is unsubstituted or substituted by:
   (a) one or more substituents independently selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide and nitrile, or
   (b) one or two aryl or heteroaryl groups.

13. The compound according to claim 1, wherein the compound is selected from the group consisting of:
   1H-imidazole-5-carboxylic acid, 4-[(4-chlorobenzoyl)amino]-2-(methylthio)-1-phenyl-, ethyl ester;
   1H-imidazole-5-carboxylic acid, 4-[(4-chlorobenzoyl)amino]-2-(methylthio)-1-phenyl-, ethyl ester;
   1H-imidazole-5-carboxylic acid, 4-[(3,4-dichlorobenzoyl)amino]-2-(methylthio)-1-(2-thienylmethyl)-, ethyl ester;
   1H-imidazole-5-carboxylic acid, 4-[(4-bromobenzoyl)amino]-2-(methylthio)-1-(phenylmethyl)-, ethyl ester;
   1H-imidazole-5-carboxylic acid, 4-[(4-chlorobenzoyl)amino]-2-(methylthio)-1-(2-thienylmethyl)-, ethyl ester;
   1H-imidazole-5-carboxylic acid, 2-(methylthio)-4-[(1-oxo-2-phenylbutyl)amino]-1-(phenylmethyl)-, ethyl ester;
   1H-imidazole-5-carboxylic acid, 4-[(4-chlorobenzoyl)amino]-2-(methylthio)-1-(phenylmethyl)-, ethyl ester;
   1H-imidazole-5-carboxylic acid, 4-[(4-methoxybenzoyl)amino]-2-(methylthio)-1-(2-thienylmethyl)-, ethyl ester;
   1H-imidazole-5-carboxylic acid, 4-[(4-methoxybenzoyl)amino]-2-(methylthio)-1-phenyl-, ethyl ester;
   1H-imidazole-5-carboxylic acid, 4-[[4-(1,1-dimethylethyl)benzoyl]amino]-2-(methylthio)-1-(phenylmethyl)-, ethyl ester;
   1H-imidazole-5-carboxylic acid, 4-[(3,4-dichlorobenzoyl)amino]-2-(methylthio)-1-(phenylmethyl)-, ethyl ester;
   1H-imidazole-5-carboxylic acid, 4-[(3,4-dichlorobenzoyl)amino]-2-(methylthio)-1-(phenylmethyl)-, ethyl ester;
   1H-imidazole-5-carboxylic acid, 4-[(4-chlorobenzoyl)amino]-1-(3-methylbutyl)-2-(methylthio)-, ethyl ester;
   1H-imidazole-5-carboxylic acid, 4-[(3,4-dichlorobenzoyl)amino]-1-(3-methylbutyl)-2-(methylthio)-, ethyl ester;
   1H-imidazole-5-carboxylic acid, 2-(methylthio)-4-[(1-oxo-2-phenoxypropyl)amino]-1-(phenylmethyl)-, ethyl ester;
   1H-imidazole-5-carboxylic acid, 2-(methylthio)-4-[(1-oxo-2-phenylbutyl)amino]-1-phenyl-, ethyl ester;
   1H-imidazole-5-carboxylic acid, 4-[(4-iodobenzoyl)amino]-2-(methylthio)-1-phenyl-, ethyl ester 1H-imidazole-5-carboxylic acid, 4-[(3,4-dichlorobenzoyl)amino]-1-(2-furanylmethyl)-2-(methylthio)-, ethyl ester;
   1H-imidazole-5-carboxylic acid, 4-[(4-chlorobenzoyl)amino]-1-(2-methoxyphenyl)-2-(methylthio)-, ethyl ester;
   1H-imidazole-5-carboxylic acid, 4-[(4-chlorobenzoyl)amino]-1-[4-(1-methylethyl)phenyl]-2-(methylthio)-, ethyl ester;
   tert-butyl 4-[(4-fluorobenzoyl)amino]-2-(methylthio)-1-phenyl-1H-imidazole-5-carboxylate;
   2-methoxy-1-methylethyl 4-[(4-chlorobenzoyl)amino]-2-(methylthio)-1-phenyl-1H-imidazole-5-carboxylate;
   cyclopentyl 4-[(4-chlorobenzoyl)amino]-2-(methylthio)-1-phenyl-1H-imidazole-5-carboxylate;
   tert-butyl 4-[(methoxyacetyl)amino]-2-(methylthio)-1-phenyl-1H-imidazole-5-carboxylate;
   isopropyl 4-[(4-chlorobenzoyl)amino]-2-(methylthio)-1-phenyl-1H-imidazole-5-carboxylate;
   2,2-dimethyipropyl 4-[(4-chlorobenzoyl)amino]-2-(methylthio)-1-phenyl-1H-imidazole-5-carboxylate;
   1-cyano-1-methylethyl 4-[(4-chlorobenzoyl)amino]-2-(methylthio)-1-phenyl-1H-imidazole-5-carboxylate;
   1,1-dimethylpentyl 4-[(4-chlorobenzoyl)amino]-2-(methylthio)-1-phenyl-1H-imidazole-5-carboxylate;
   tetrahydrofuran-3-yl 4-[(4-chlorobenzoyl)amino]-2-(methylthio)-1-phenyl-1H-imidazole-5-carboxylate;
   2-methoxy-1,1-dimethylethyl 4-[(4-chlorobenzoyl)amino]-2-(methylthio)-1-phenyl-1H-imidazole-5-carboxylate;
   1,1-dimethyl-2-oxopropyl 4-[(4-chlorobenzoyl)amino]-2-(methylthio)-1-phenyl-1H-imidazole-5-carboxylate;
   1-(methoxymethyl)propyl 4-[(4-chlorobenzoyl)amino]-2-(methylthio)-1-phenyl-1H-imidazole-5-carboxylate;
   2-methoxy-1,1-dimethylethyl 4-[(2,3-dihydro-1,4-benzodioxin-2-ylcarbonyl)amino]-2-methoxy-1-pheny1-1H-imidazo1e-5-carboxylate;
   2-methoxy-1,1-dimethylethyl 4-{[(3-chlorophenoxy)acetyl]amino }-2-methoxy-1-phenyl-1H-imidazole-5-carboxylate;
   2-methoxy-1,1-dimethylethyl 4-[(4-chlorobenzoyl)amino]-2-methoxy-1-phenyl-1H-imidazole-5-carboxylate;
   2-methoxy-1,1-dimethylethyl 4-[(2,4-dichlorobenzoyl)amino]-2-methoxy-1-phenyl-1H-imidazole-5-carboxylate.

14. A method for modulating a positive allosteric $GABA_B$ receptor, the method comprising administering the compound according to claim 1 to a patient in need thereof.

15. A pharmaceutical composition comprising the compound according to claim 1 as active ingredient and a pharmaceutically acceptable carrier or diluent.

16. A method for the treatment of gastroesophageal reflux disease (GERD), the method comprising administering a therapeutically effective amount of the compound according to claim 1, optionally in combination with a $GABA_B$ receptor agonist, to a patient in need thereof.

17. A method for the treatment of reflux, the method comprising administering a therapeutically effective amount of the compound according to claim 1, optionally in combination with a $GABA_B$ receptor agonist, to a patient in need thereof.

18. A method for the treatment of transient lower esophageal sphincter relaxations (TLESRs), the method comprising administering a therapeutically effective amount of the compound according to claim 1, optionally in combination with a $GABA_B$ receptor agonist, to a patient in need thereof.

19. A method for the treatment of a functional gastrointestinal disorder, the method comprising administering a therapeutically effective amount of the compound according to claim 1, optionally in combination with a $GABA_B$ receptor agonist, to a patient in need thereof.

20. The method according to claim 19, wherein the functional gastrointestinal disorder is functional dyspepsia.

21. A method for the treatment of irritable bowel syndrome (IBS), the method comprising administering a therapeutically effective amount of the compound according to claim 1, optionally in combination with a $GABA_B$ receptor agonist, to a patient in need thereof.

22. The method according to claim 21, wherein the IBS is constipation predominant IBS.

23. The method according to claim 21 wherein the IBS is diarrhea predominant IBS.

24. The method according to claim 21 wherein the IBS is alternating bowel movement predominant IBS.

25. A process for the preparation of a compound according to claim 1, the process comprising one or more steps selected from the group consisting of:

a) treating dimethylcyanodithioimidocarbonate with an amine to obtain a compound of formula (IV);

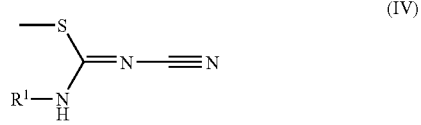

b) replacing the thiomethoxy substituent of compound (IV) with a $C_1$-$C_7$ alkoxy group to obtain a compound of formula (III);

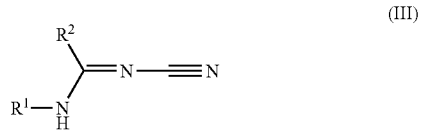

c) reacting a compound of formula (III) or (IV) with an alpha halo carbonyl compound to obtain an aminoimidazole compound of formula II; and

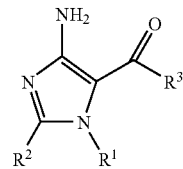

d) reacting the compound of formula II with an acyl chloride to obtain the compound of formula I,
wherein $R^1$-$R^4$ are as defined in claim 1.

26. A compound of formula II,

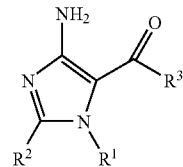

wherein,
$R^1$ is selected from the group consisting of:
(a) $C_1$-$C_{10}$ alkyl, $C_2$-$C_{10}$ alkenyl, $C_2$-$C_{10}$ alkynyl, and $C_3$-$C_{10}$ cycloalkyl, and is unsubstituted or substituted by:
(I) one or more substituents selected from the group consisting of $C_1$-$C_{10}$ alkoxy, $C_3$-$C_{10}$ cycloalkyl, $C_1$-$C_{10}$ thioalkoxy, halogen, hydroxy, mercapto, carboxylic acid, carboxylic acid ester, carboxylic acid amide, and nitrile, or
(ii) one or two aryl or heteroaryl groups and
(b) aryl or heteroaryl, each of which is independently unsubstituted or substituted by:
(i) one or more substituents selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide and nitrile, or
(ii) one or two aryl or heteroaryl groups;
$R^2$ is $C_1$-$C_{10}$ alkoxy or $C_1$-$C_{10}$ thioalkoxy, and is unsubstituted or substituted by:
(a) one or more substituents selected from the group consisting of $C_1$-$C_{10}$ thioalkoxy, halogen, hydroxy, mercapto, carboxylic acid, carboxylic acid ester, carboxylic acid amide, and nitrile; or
(b) one or two aryl or heteroaryl groups;
$R^3$ is selected from the group consisting of:
(a) $C_1$-$C_{10}$ alkoxy, which is unsubstituted or substituted by:
(i) one or more substituents selected from the group consisting of $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, and nitrile, or
(ii) one or two aryl or heteroaryl groups;
(b) $C_1$-$C_{10}$ alkyl, $C_2$-$C_{10}$ alkenyl, $C_2$-$C_{10}$ alkynyl, and $C_3$-$C_{10}$ cycloalkyl, which is unsubstituted or substituted by:
(i) one or more substituents selected from the group consisting of $C_1$-$C_{10}$ alkoxy, $C_1$-$C_{10}$ thioalkoxy, $C_3$-$C_{10}$ cycloalkyl, keto, halogen, hydroxy, mercapto, carboxylic acid, carboxylic acid ester, carboxylic acid amide, and nitrile, or
  (ii) one or two aryl or heteroaryl groups;
(c) aryl or heteroaryl, each of which is unsubstituted or substituted by:
  (i) one or more substituents selected the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_{10}$ alkoxy, $C_1$-$C_{10}$ thioalkoxy, halogen, hydroxy, mercapto, nitro, keto, carboxylic acid, carboxylic acid ester, carboxylic acid amide, and nitrile, or
  (ii) one or two aryl or heteroaryl groups; and
(d) amino, which is unsubstituted or mono- or disubstituted with substituents independently selected from the group consisting of $C_1$-$C_{10}$ alkyl, $C_2$-$C_{10}$ alkenyl, $C_2$-$C_{10}$ alkynyl, and $C_3$-$C_{10}$ cycloalkyl;

wherein any of the alkyl, alkenyl, alkynyl and cycloalkyl substituents of $R^1$-$R^4$ may independently have one or more carbon atom(s) substituted by O, N or S;

with the proviso that the compound of formula II is not:
1H-imidazole-5-carboxylic acid, 4-amino-1-methyl-2-(methylthio)-, ethyl ester;
ethyl-4-amino-1-(2-furylmethyl)-2-(methylthio)-1H-imidazole-5-carboxylate;
ethyl-4-amino-1-(4-isopropylphenyl)-2-(methylthio)-1H-imidazole-5-carboxylate;
ethyl-4-amino-1-(2-methoxyphenyl)-2-(methylthio)-1H-imidazole-5-carboxylate;
methanone, [4-amino-1-methyl-2-(methylthio)-1H-imidazole-5-yl]phenyl;
methanone, [4-amino-2-(methylthio)-1-phenyl-1H-imidazol-5-yl]phenyl-;
1H-imidazole-5-carboxylic acid, 4-amino-2-(methylthio)-1-phenyl-, ethyl ester;
1H-imidazole-5-carboxylic acid, 4-amino-1-methyl-2-(methylthio)-, ethyl ester;
1H-imidazole-5-carboxylic acid, 4-amino-2-(methylthio)-1-(2-propenyl)-, ethyl ester.

* * * * *

UNITED STATES PATENT AND TRADEMARK OFFICE
CERTIFICATE OF CORRECTION

PATENT NO. : 7,718,686 B2  
APPLICATION NO. : 11/570830  
DATED : May 18, 2010  
INVENTOR(S) : Bauer et al.

Page 1 of 1

It is certified that error appears in the above-identified patent and that said Letters Patent is hereby corrected as shown below:

Col. 75:  
Claim 1, line 21: Line should read: "(a) $C_1$-$C_{10}$ alkyl, $C_2$-$C_{10}$ alkenyl, $C_2$-$C_{10}$ alkynyl, $C_1$-$C_{10}$ alkoxy", and".

Col. 78:  
Claim 13, line 58: Insert --and-- after the full name of the compound.

Col. 82:  
Claim 26, line 18: Insert --or-- after the full name of the compound.

Signed and Sealed this

Twenty-seventh Day of July, 2010

David J. Kappos  
*Director of the United States Patent and Trademark Office*